(12) United States Patent
Salazar et al.

(10) Patent No.: US 11,602,619 B2
(45) Date of Patent: Mar. 14, 2023

(54) COUPLING ASSEMBLY FOR VARIABLE DIAMETER SURGICAL INSTRUMENT

(71) Applicants: Acclarent, Inc., Irvine, CA (US); Biosense Webster (Israel) Ltd., Yokneam (IL)

(72) Inventors: Henry F. Salazar, Pico Rivera, CA (US); Athanasios Papadakis, Newport Beach, CA (US); Jetmir Palushi, Irvine, CA (US); Christopher T. Beeckler, Brea, CA (US); Fatemeh Akbarian, Rancho Palos Verdes, CA (US); Marc Dean, Fort Worth, TX (US); Julie M. Taylor, Yorba Linda, CA (US); Ehsan Shameli, Irvine, CA (US); John H. Thinnes, Jr., Mission Viejo, CA (US); Yehuda Algawi, Binyamina (IL); Krishna Murthy Rajan, Irvine, CA (US); Babak Ebrahimi, Irvine, CA (US)

(73) Assignees: Biosense Webster (Israel) Ltd., Yokneam (IL); Acclarent, Inc., Irvine, CA (US)

( * ) Notice: Subject to any disclaimer, the term of this patent is extended or adjusted under 35 U.S.C. 154(b) by 699 days.

(21) Appl. No.: 16/556,283

(22) Filed: Aug. 30, 2019

(65) Prior Publication Data
US 2020/0108236 A1    Apr. 9, 2020

Related U.S. Application Data

(60) Provisional application No. 62/825,847, filed on Mar. 29, 2019, provisional application No. 62/781,667,
(Continued)

(51) Int. Cl.
| | | |
|---|---|---|
| A61M 29/00 | (2006.01) | |
| A61M 25/06 | (2006.01) | |
| A61B 17/24 | (2006.01) | |

(52) U.S. Cl.
CPC ........ A61M 29/00 (2013.01); A61M 25/0662 (2013.01); *A61B 17/24* (2013.01); *A61M 2025/0681* (2013.01)

(58) Field of Classification Search
CPC .............. A61M 29/00; A61M 25/0662; A61M 2025/0681; A61M 25/0113;
(Continued)

(56) References Cited

U.S. PATENT DOCUMENTS

| | | |
|---|---|---|
| 703,229 A | 6/1902 | Boman |
| 930,695 A | 8/1909 | Royle |
(Continued)

FOREIGN PATENT DOCUMENTS

| | | |
|---|---|---|
| CN | 103124531 A | 5/2013 |
| CN | 106580375 A | 4/2017 |
(Continued)

OTHER PUBLICATIONS

International Search Report and Written Opinion dated Jan. 2, 2020 for Application No. PCT/IB2019/058350, 15 pgs.
(Continued)

*Primary Examiner* — Amber R Stiles
(74) *Attorney, Agent, or Firm* — Frost Brown Todd LLP

(57) ABSTRACT

An apparatus may be used with an elongate member that includes an engagement member, a hollow shaft, a compression member, a compression element, and a resilient gripping member. The hollow shaft extends from the engagement member along a longitudinal axis. The compression member is slidably disposed over the hollow shaft. The hollow shaft is disposed over the resilient gripping
(Continued)

member and supports the compression element. The compression member has a conical inner surface including a detent feature. The conical inner surface is configured to urge the compression element radially inwards as the collar advances from the unlocked position toward the locked position where the detent feature retains the compression element. The compression element deforms the resilient gripping member radially inwards to grip the elongate member and prevents translation of the elongate member. When unlocked, the resilient gripping member moves radially away from the elongate member allowing translation.

20 Claims, 25 Drawing Sheets

Related U.S. Application Data filed on Dec. 19, 2018, provisional application No. 62/741,611, filed on Oct. 5, 2018.

(58) Field of Classification Search
CPC .. A61M 25/09041; A61M 2025/09125; A61M 39/286; A61M 39/28; A61B 17/24; A61B 2017/22049
See application file for complete search history.

(56) References Cited

U.S. PATENT DOCUMENTS

| | | |
|---|---|---|
| 3,550,861 A | 12/1970 | Teson |
| 3,762,732 A | 10/1973 | Speed |
| 4,013,310 A | 3/1977 | Dye |
| 4,243,034 A * | 1/1981 | Brandt ................ A61M 39/286 251/6 |
| 4,525,111 A | 6/1985 | Gutsche |
| 5,125,915 A | 6/1992 | Berry et al. |
| 5,851,189 A | 12/1998 | Forber |
| 5,947,484 A | 9/1999 | Huggins et al. |
| 6,234,491 B1 | 5/2001 | Wheeler |
| 6,932,795 B2 | 8/2005 | Lopez et al. |
| 7,328,903 B2 | 2/2008 | Casel |
| 9,095,646 B2 | 8/2015 | Chow et al. |
| 9,155,492 B2 | 10/2015 | Jenkins et al. |
| 9,962,530 B2 | 5/2018 | Johnson et al. |
| 10,071,235 B1 | 9/2018 | Narciso-Martinez et al. |
| 2002/0062106 A1 | 5/2002 | Chu et al. |
| 2007/0171540 A1 | 7/2007 | Veldman et al. |
| 2010/0211006 A1 | 8/2010 | Schmidt-Sørensen |
| 2010/0274188 A1 | 10/2010 | Chang et al. |
| 2011/0004057 A1 | 1/2011 | Goldfarb et al. |
| 2012/0041426 A1 | 2/2012 | Bizup |
| 2013/0274715 A1 | 10/2013 | Chan et al. |
| 2014/0364725 A1 | 12/2014 | Makower |
| 2015/0174372 A1 | 6/2015 | Kaiser |
| 2016/0008083 A1 | 1/2016 | Kesten et al. |
| 2016/0058985 A1 | 3/2016 | Lam et al. |
| 2017/0238822 A1 | 8/2017 | Young et al. |
| 2018/0028339 A1 | 2/2018 | Loper et al. |
| 2018/0133440 A1 | 5/2018 | Chrisman |
| 2018/0214216 A1 | 8/2018 | Sema et al. |
| 2018/0310886 A1 | 11/2018 | Salazar et al. |
| 2019/0015645 A1 | 1/2019 | Matlock et al. |
| 2019/0192177 A1 | 6/2019 | Palushi et al. |
| 2019/0274701 A1 | 9/2019 | Hamlekhan et al. |

FOREIGN PATENT DOCUMENTS

| | | |
|---|---|---|
| CN | 207071112 U | 3/2018 |
| GB | 1428922 A | 3/1976 |
| WO | WO 93/06878 A1 | 4/1993 |
| WO | WO 2016/007166 A1 | 1/2016 |

OTHER PUBLICATIONS

Chinese Office Action and Search Report dated Jun. 29, 2022, for Application No. 201980065136.1, 15 pages.

* cited by examiner

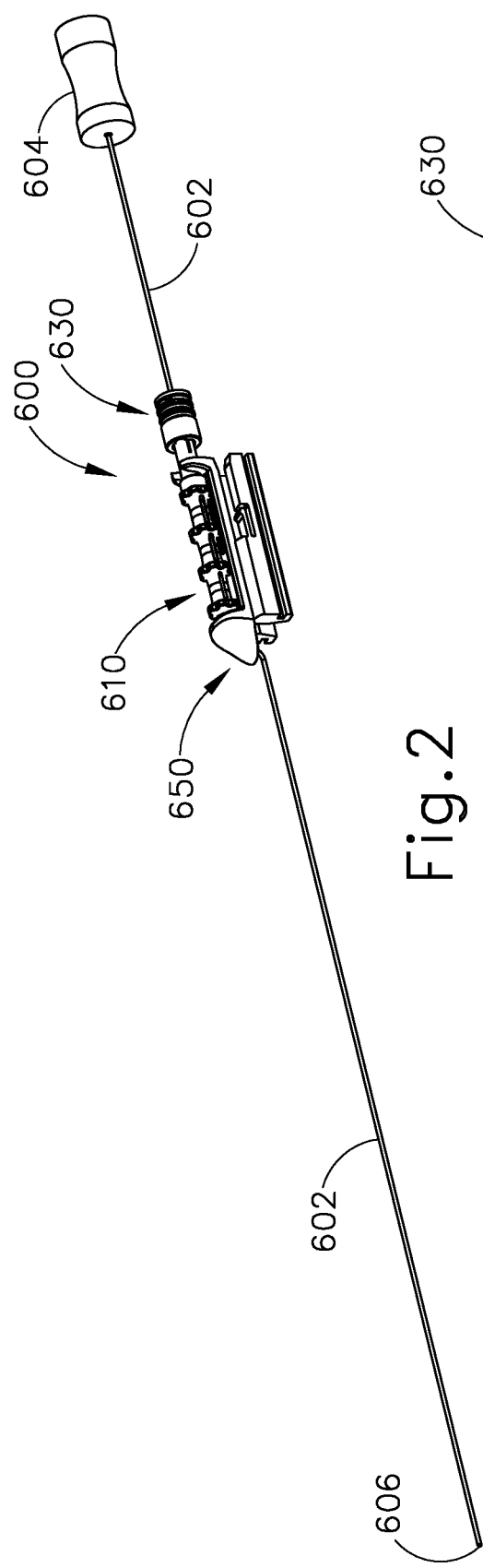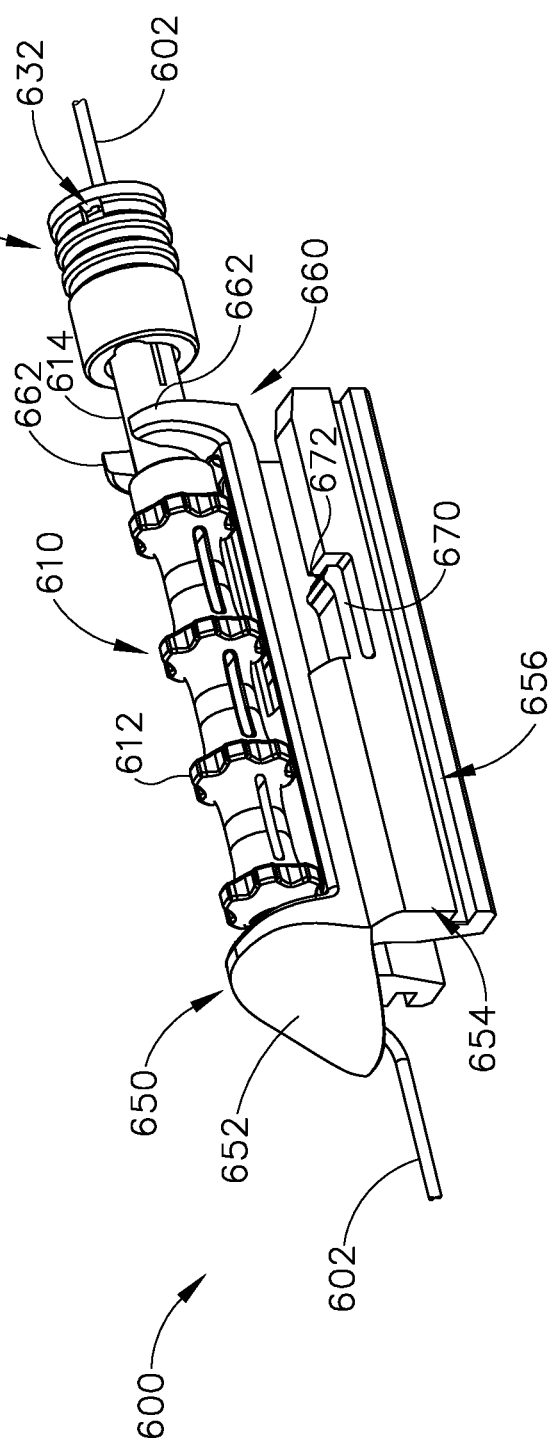

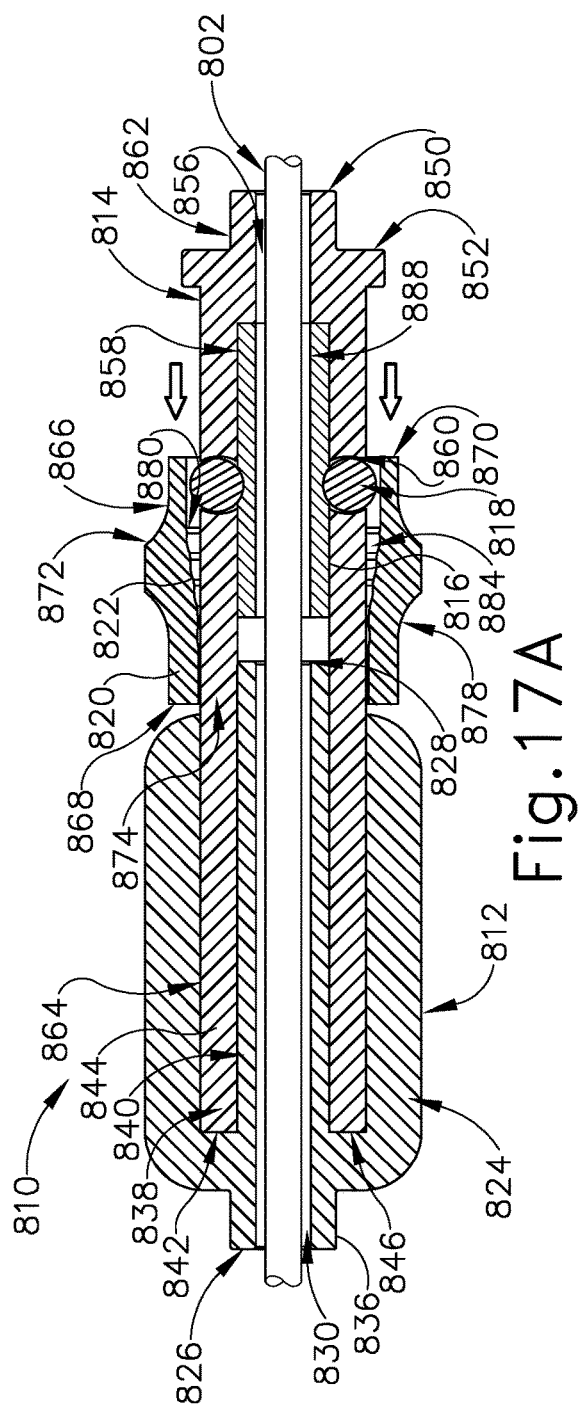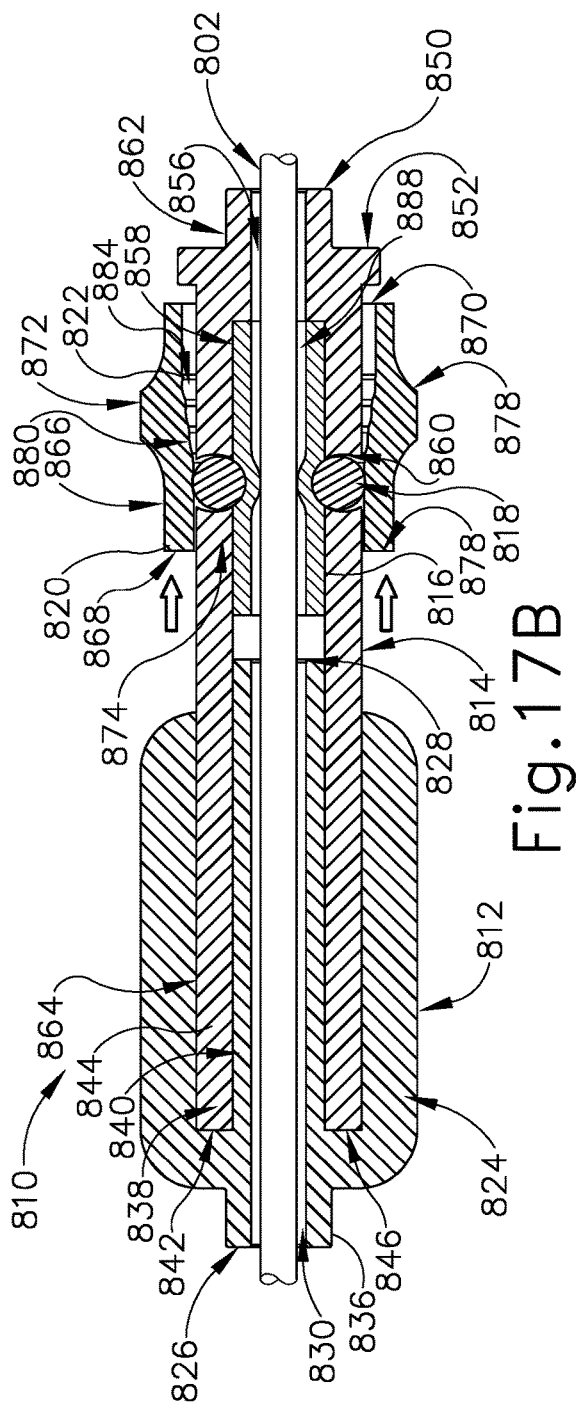
Fig.17A
Fig.17B

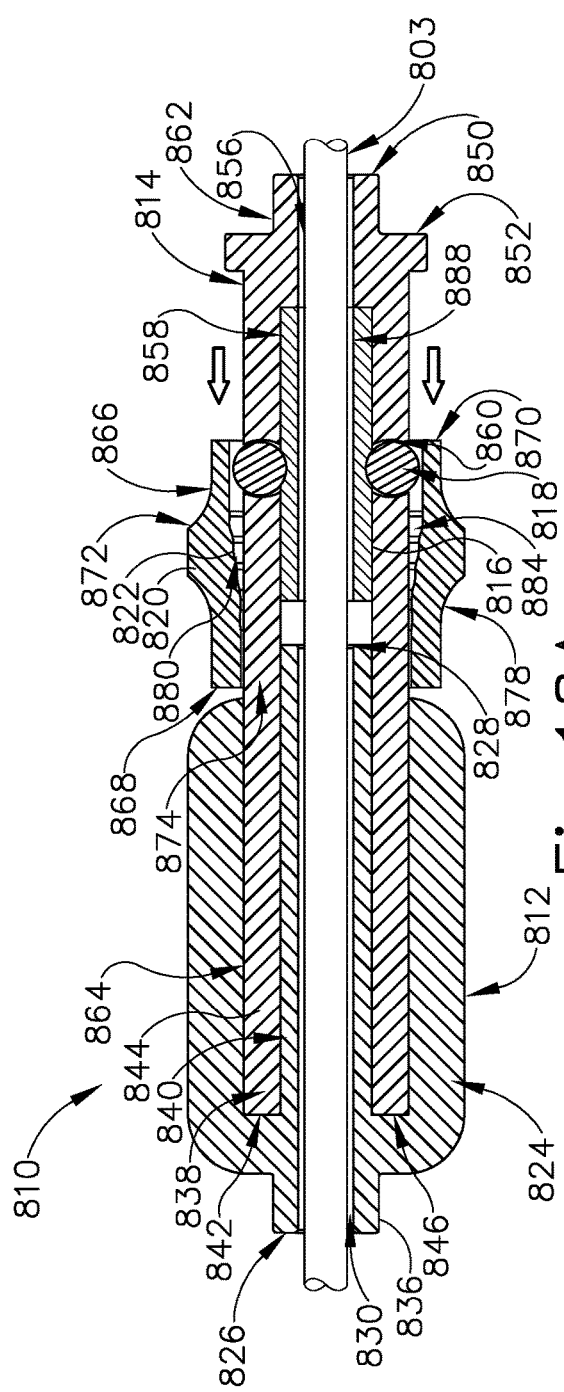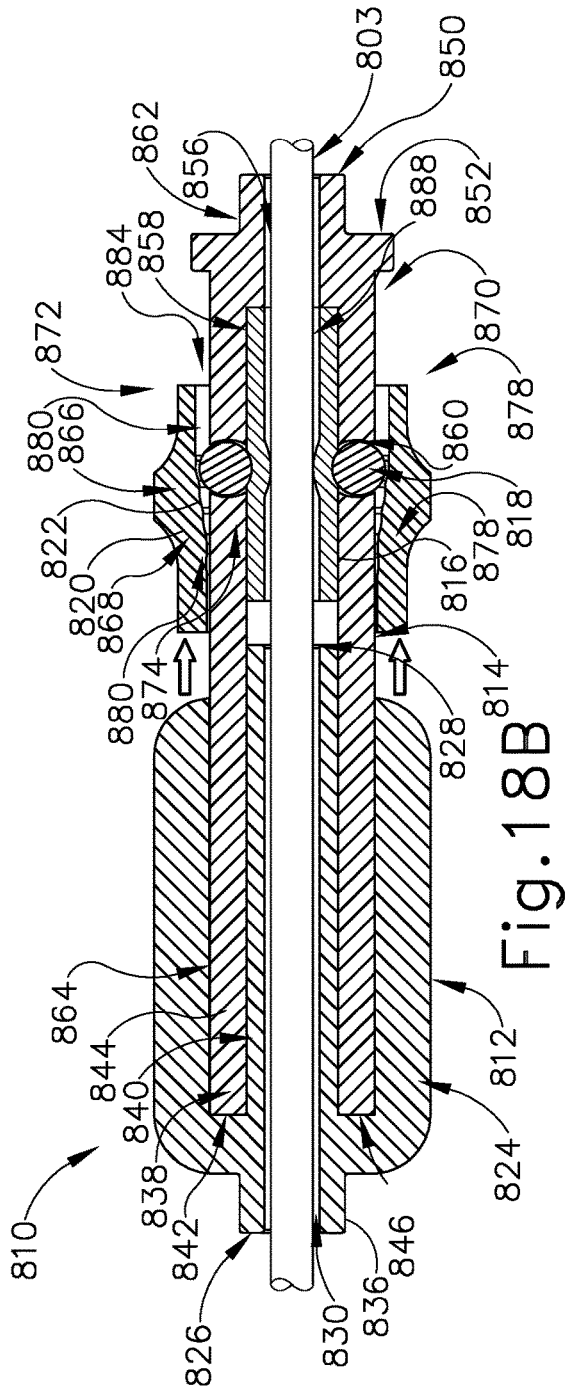

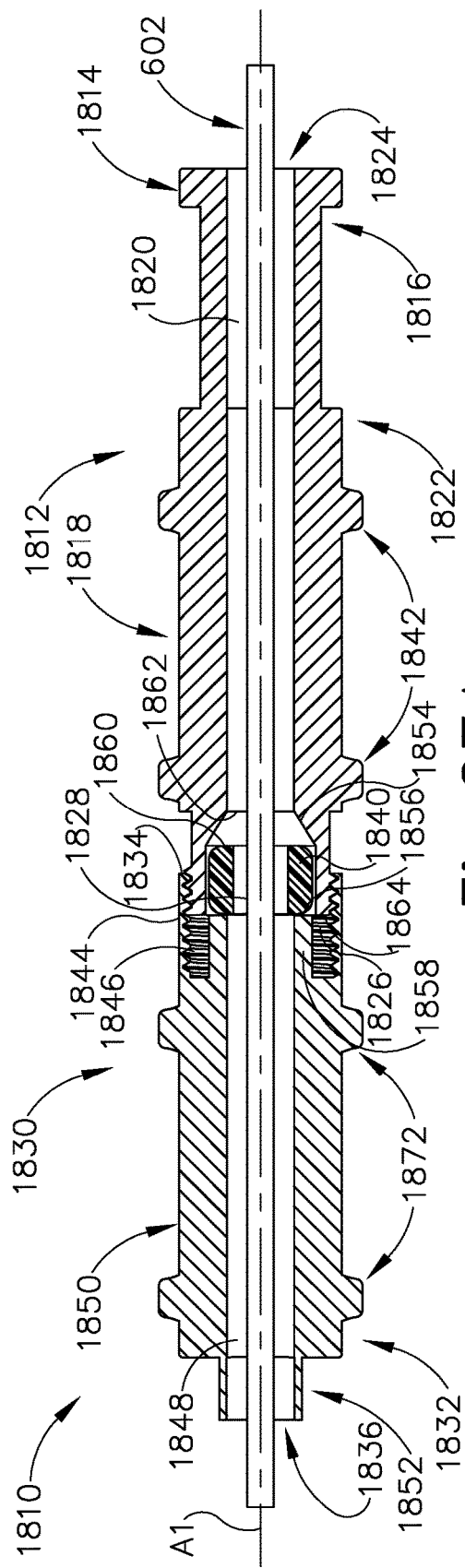
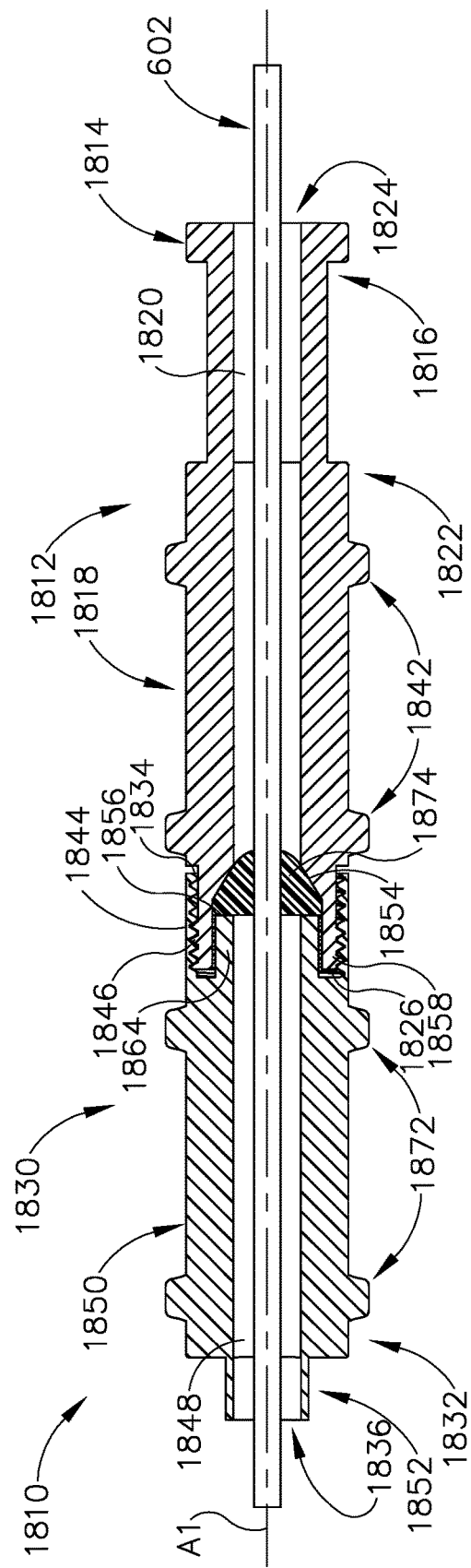

COUPLING ASSEMBLY FOR VARIABLE DIAMETER SURGICAL INSTRUMENT

PRIORITY

This application claims priority to U.S. Provisional Pat. App. No. 62/741,611, entitled "Coupling Assembly for Variable Diameter Surgical Instrument," filed Oct. 5, 2018, the disclosure of which is incorporated by reference herein in its entirety.

This application also claims priority to U.S. Provisional Pat. App. No. 62/781,667, entitled "Locking Mechanism for Variable Diameter Surgical Instrument," filed Dec. 19, 2018, the disclosure of which is incorporated by reference herein in its entirety.

This application also claims priority to U.S. Provisional Pat. App. No. 62/825,847, entitled "Quick Release Mechanism for Variable Diameter Surgical Instrument," filed Mar. 29, 2019, the disclosure of which is incorporated by reference herein in its entirety.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, now abandoned, entitled "Systems and Methods for Transnasal Dilation of Passageways in the Ear, Nose or Throat," published Jan. 6, 2011, the disclosure of which is incorporated by reference herein in its entirety. An example of such a system is the Relieva Spin Balloon Sinuplasty System by Acclarent, Inc. of Irvine, Calif.

In the context of Eustachian tube dilation, a dilation catheter or other dilation instrument may be inserted into the Eustachian tube and then be inflated or otherwise expanded to thereby dilate the Eustachian tube. The dilated Eustachian tube may provide improved ventilation from the nasopharynx to the middle ear and further provide improved drainage from the middle ear to the nasopharynx. Methods and devices for dilating the Eustachian tube are disclosed in U.S. Patent Pub. No. 2010/0274188, entitled "Method and System for Treating Target Tissue within the ET," published on Oct. 28, 2010, now abandoned, the disclosure of which is incorporated by reference herein; and U.S. Patent Pub. No. 2013/0274715, entitled "Method and System for Eustachian Tube Dilation," published on Oct. 17, 2013, now abandoned, the disclosure of which is incorporated by reference herein in its entirety. An example of such a system is the Aera® Eustachian Tube Balloon Dilation System by Acclarent, Inc. of Irvine, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pat. No. 9,155,492, entitled "Sinus Illumination Lightwire Device," issued Oct. 13, 2015, the disclosure of which is incorporated by reference herein in its entirety. An example of such an illuminating guidewire is the Relieva Luma Sentry® Sinus Illumination System by Acclarent, Inc. of Irvine, Calif.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation systems that may be used in IGS procedures is the CARTO® 3 System by Biosense-Webster, Inc., of Irvine, Calif. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

An example of an electromagnetic IGS systems that may be used in ENT and sinus surgery is the CARTO® 3 System by Biosense-Webster, Inc., of Irvine, Calif. When applied to functional endoscopic sinus surgery (FESS), balloon sinuplasty, and/or other ENT procedures, the use of IGS systems allows the surgeon to achieve more precise movement and positioning of the surgical instruments than can be achieved by viewing through an endoscope alone. As a result, IGS systems may be particularly useful during performance of FESS, balloon sinuplasty, and/or other ENT procedures where anatomical landmarks are not present or are difficult to visualize endoscopically. In order to enable use of an IGS system in an ENT procedure, the instrumentation used in the ENT procedure may include a guidewire that has a position sensor that cooperates with the IGS system to provide data indicating the position of the distal end of the guidewire in real time. Such an IGS system navigation guidewire may be used in addition to, or in lieu of, the navigating guidewire referred to above. Examples of use of an IGS system in an ENT procedure are described in U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein; and U.S. Pub. No. 2018/0310886, entitled "Apparatus to Secure Field Generating Device to Chair," published Nov. 1, 2018, issued as U.S. Pat. No. 10,561,370 on Feb. 18, 2020, the disclosure of which is incorporated by reference herein in its entirety.

While several systems and methods have been made and used to position a balloon of a dilation catheter in an anatomical passageway, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 2 depicts a perspective view of a guidewire actuation assembly of the dilation instrument of FIG. 1A;

FIG. 3 depicts an enlarged perspective view of actuators of the guidewire actuation assembly of FIG. 2, with a collet collar in a proximal position;

FIG. 17A depicts a cross-sectional view of the guidewire actuation mechanism of FIG. 6 being transitioned into the unlocked state about a first received elongate member having a first outer diameter;

FIG. 17B depicts a cross-sectional view of the guidewire actuation mechanism of FIG. 6 being transitioned into the locked state about the first received elongate member of FIG. 17A;

FIG. 18A depicts a cross-sectional view of the guidewire actuation mechanism of FIG. 6 being transitioned into the unlocked state about a second received elongate member having a second outer diameter;

FIG. 18B depicts a cross-sectional view of the guidewire actuation mechanism of FIG. 6 being transitioned into the locked state about the second received elongate member of FIG. 18A;

FIG. 27A depicts a cross-sectional view of the guidewire actuation mechanism of FIG. 21, with the guidewire actuation mechanism in a guidewire-releasing state; and FIG. 27B depicts a cross-sectional view of the guidewire actuation mechanism of FIG. 21, with the second member rotated relative to the first member to transition the guidewire actuation mechanism into a guidewire-gripping state.

Figure 1A:
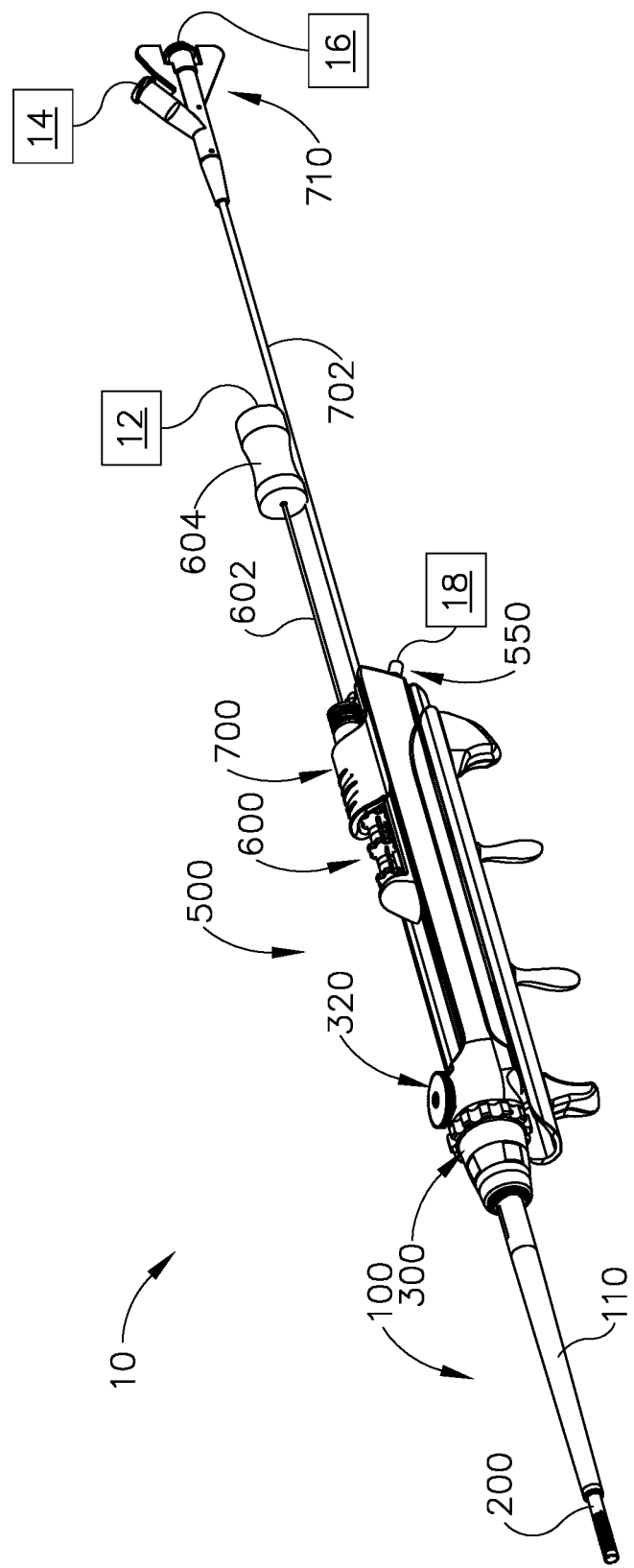
FIG. 1A depicts a perspective view of an exemplary dilation instrument, with a guidewire and a dilation catheter of the instrument each in respective proximal positions.
Figure 1B:
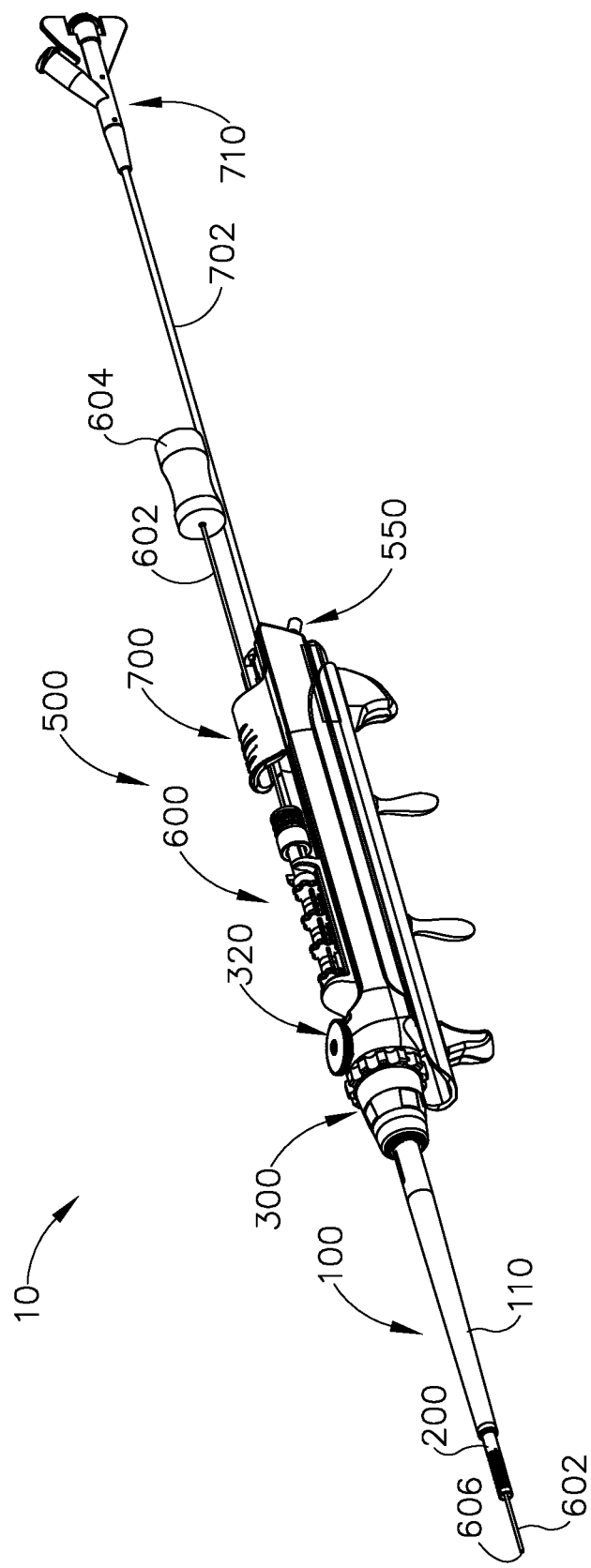
FIG. 1B depicts a perspective view of the dilation instrument of FIG. 1A, with the guidewire in a distal position and the dilation catheter in the proximal position.
Figure 1C:
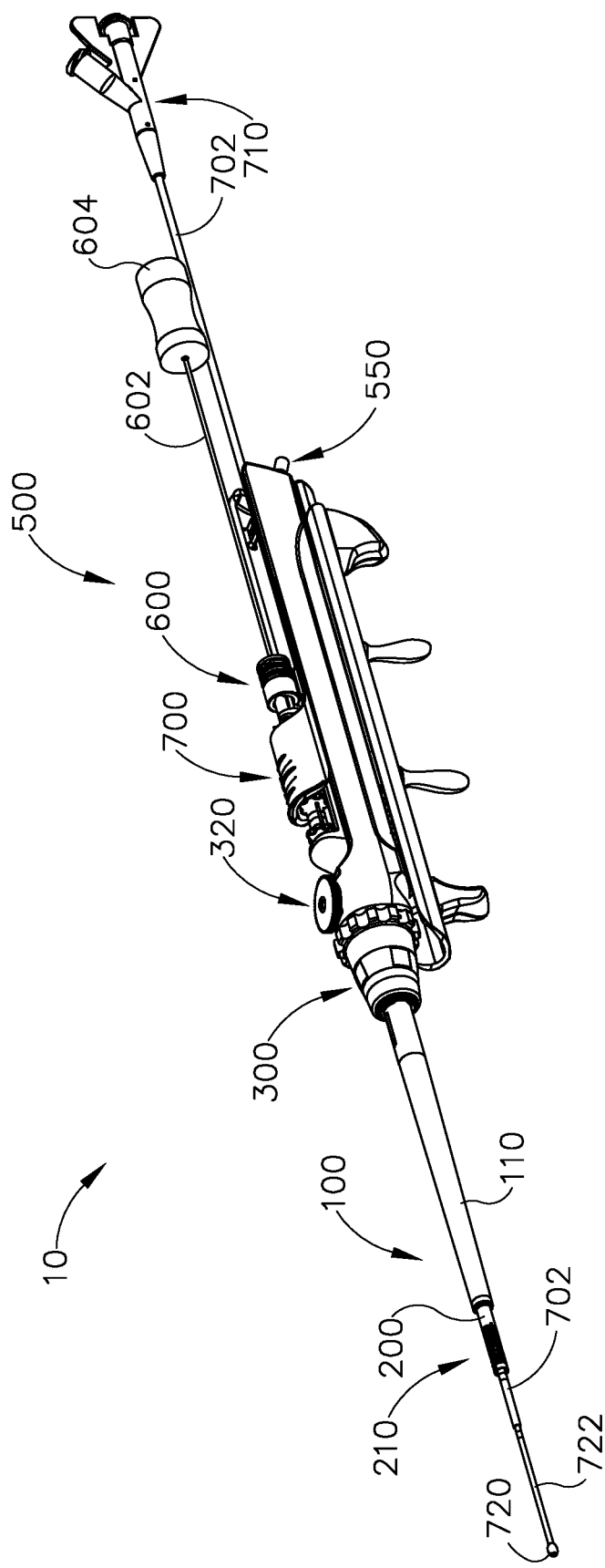
FIG. 1C depicts a perspective view of the dilation instrument of FIG. 1A, with the guidewire and the dilation catheter each in respective distal positions, and with a dilator of the dilation catheter in a non-expanded state.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "circumferentially" and "radially" also are used herein with respect to the longitudinal axis. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. EXEMPLARY DILATION INSTRUMENT OVERVIEW

FIGS. 1A-1D show an exemplary dilation instrument (10) that may be used to dilate the ostium of a paranasal sinus, to dilate another passageway associated with drainage of a paranasal sinus, to dilate a Eustachian tube, or to dilate some other anatomical passageway (e.g., within the ear, nose, or throat, etc.). Dilation instrument (10) of the present example provides adjustability that enables the operator to use dilation instrument (10) in different scenarios, without requiring the operator to switch between different instruments. For instance, dilation instrument (10) may be used to dilate various different anatomical passageways (e.g., frontal sinus ostium, frontal recess, maxillary sinus ostium, sphenoid sinus ostium, ethmoid sinus ostium, Eustachian tube, etc.) by making simple adjustments to structural features of the instrument.

A. Overview of Dilation Instrument

Dilation instrument (10) of this example includes a handle assembly (500), a guide shaft assembly (100) extending distally from handle assembly (500); a guidewire actuation assembly (600) slidably coupled with handle assembly (500); and a dilation catheter actuation assembly (700) slidably coupled with handle assembly (500). A guidewire module (12) (FIG. 1A) is coupled with a guidewire (602) of dilation instrument (10) via a connector (604). An inflation fluid source (14) and an irrigation fluid source (16) are coupled with a dilation catheter (702) of dilation instrument (10) via a connector (710). A suction source (18) is coupled with a suction conduit (not shown) of dilation instrument (10) via a suction port (550).

Handle assembly (500) is sized and configured to be grasped and operated by a single hand of an operator. The operator may selectively operate guidewire actuation assembly (600) and dilation catheter actuation assembly (700) with the same single hand that grasps handle assembly (500). As shown in the transition from FIG. 1A to FIG. 1B, the operator may advance guidewire actuation assembly (600) distally along handle assembly (500) to thereby advance guidewire (602) distally, such that distal end (606) of guidewire (602) is positioned distal to distal end of guide shaft assembly (100). As shown in the transition from FIG. 1B to FIG. 1C, the operator may advance dilation catheter actuation assembly (700) distally along handle assembly (500) to thereby advance dilation catheter (702) distally, such that distal tip (720) of dilation catheter (702) is positioned distal to distal end of guide shaft assembly (100). With dilation catheter (702) advanced to a distal position, the operator may then inflate a dilator (722) of dilation catheter (702) to achieve an expanded state as shown in FIG. 1D, to thereby dilate an anatomical passageway in which dilator (722) is positioned.

Guide shaft assembly (100) of this example includes a rigid shaft member (110), a flexible shaft member (200), and a deflection control knob (300). Deflection control knob (300) is operable to cause guide shaft assembly (100) to flex laterally at flexible guide shaft member (200), to thereby allow the operator to vary the exit angle of dilation catheter (702) relative to the longitudinal axis of rigid shaft member (110). A rotation control knob (320) is operable to rotate guide shaft assembly (100) about the longitudinal axis of rigid shaft member (110), thereby providing additional control to the operator to facilitate access to various anatomical passageways within the head of a patient.

In the present example, dilation catheter (702) is coaxially disposed within guide shaft assembly (100), and guidewire (602) is coaxially disposed within dilation catheter (702). In some other versions, guide shaft assembly (100) is coaxially disposed within dilation catheter (702), and guidewire (602) is coaxially disposed within guide shaft assembly (100). Also, in some versions, guidewire (602) is omitted.

Figure 1D:
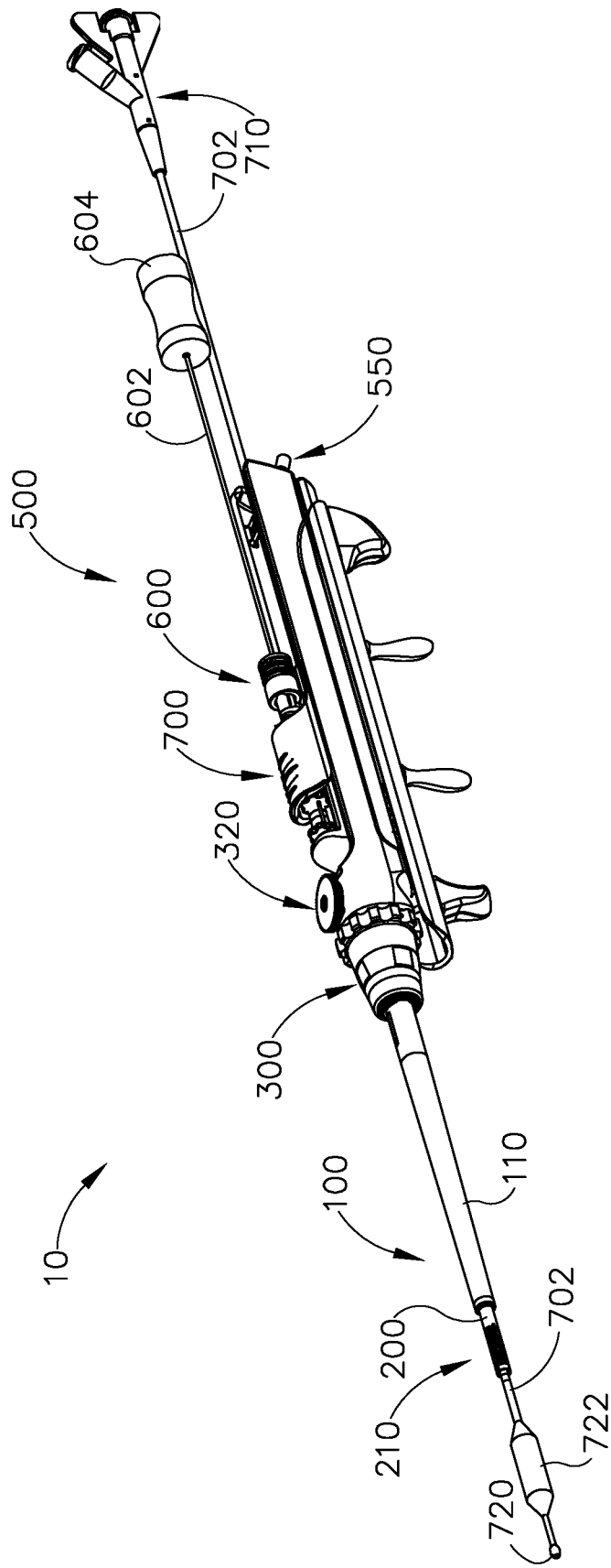
FIG. 1D depicts a perspective view of the dilation instrument of FIG. 1A, with the guidewire and the dilation catheter each in respective distal positions, and with a dilator of the dilation catheter in an expanded state.

As shown in FIG. 1A, the proximal end of dilation catheter (702) includes a connector (710) that is configured to couple with an inflation fluid source (14) and an irrigation fluid source (16). By way of example only, connector (710) may be connected and operable in accordance with at least some of the teachings of U.S. patent application Ser. No. 16/247,739, entitled "Fluid Fitting for Dilation Instrument," filed Jan. 15, 2019, issued as U.S. Pat. No. 11,272,946 on Mar. 15, 2022, the disclosure of which is incorporated by reference herein in its entirety. Inflation fluid source (14) (FIG. 1A) is operable to provide an inflation fluid (e.g., saline) via connector (710) to selectively inflate and deflate dilator (722) of dilation catheter (702). In some versions, inflation fluid source (14) is constructed and operable in accordance with at least some of the teachings of U.S. Pat. No. 9,962,530, entitled "Inflator for Dilation of Anatomical Passageway," issued May 8, 2018, the disclosure of which is incorporated by reference herein in its entirety. As another merely illustrative example, inflation fluid source (14) may be constructed and operable in accordance with at least some of the teachings of U.S. Pub. No. 2016/0058985, entitled "Automated Inflator for Balloon Dilator," published Mar. 3, 2016, now abandoned, the disclosure of which is incorporated by reference herein in its entirety. Other suitable forms that inflation fluid source (14) may take will be apparent to those skilled in the art in view of the teachings herein.

In addition to being capable of providing dilation, dilation catheter (702) of the present example is also configured to provide irrigation of a site within a patient. By way of example only, dilation catheter (702) may be constructed and operable in accordance with at least some of the teachings of U.S. Pat. No. 9,095,646, entitled "Devices and Methods for Transnasal Dilation and Irrigation of the Sinuses," issued Aug. 4, 2015, the disclosure of which is incorporated by reference herein in its entirety. Dilation catheter (702) receives irrigation fluid (e.g., saline) from irrigation fluid source (16) via connector (710) of connector (710) as described above. By way of example only, irrigation fluid source (16) may provide gravity-fed irrigation fluid, may include a syringe, may include an electrically activated pump, or may take any other suitable form as will be apparent to those skilled in the art in view of the teachings herein.

By way of further example only, dilation instrument (10) may be further configured and operable in accordance with the teachings of U.S. Pub. No. 2019/0015645, entitled "Adjustable Instrument for Dilation of Anatomical Passageway," published Jan. 17, 2019, issued as U.S. Pat. No. 10,874,839 on Dec. 29, 2020, the disclosure of which is incorporated by reference herein; or in accordance with the teachings of any other patent reference cited herein. Other variations of the features and functionalities described herein will be apparent to those skilled in the art in view of the teachings herein.

B. Exemplary Guidewire and Associated Actuation Assembly of Dilation Instrument

FIGS. 2-5 show various components of guidewire actuation assembly (600) in greater detail. These components include a spin actuator (610) and a slide actuator (650). Spin actuator (610) is operable to rotate guidewire (602) relative to handle assembly (500) (FIG. 1A), about longitudinal axis of guidewire (602); while slide actuator (650) is operable to translate guidewire (602) relative to handle assembly (500), along the longitudinal axis of guidewire (602).

In some versions, guidewire (602) includes one or more optical fibers and a distal end (606) that is configured to emit visible light. In some such versions, guidewire module (12) (FIG. 1A) includes a light source, and connector (604) is operable to communicate light from the light source of guidewire module (12) to guidewire (602). Illuminating versions of guidewire (602) may be used to provide position confirmation through observation of transillumination effects. By way of example only, illuminating versions of guidewire (602) may be constructed and operable in accordance with at least some of the teachings of U.S. Pat. No. 9,155,492, entitled "Sinus Illumination Lightwire Device," issued Oct. 13, 2015, the disclosure of which is incorporated by reference herein in its entirety.

In addition to providing illumination, or as an alternative to providing illumination, guidewire (602) may provide position sensing capabilities. In some such versions, the distal end of guidewire (602) may include a position sensor. By way of example only, such a guidewire (602) may be constructed and operable in accordance with at least some of the teachings of U.S. Pub. No. 2018/0214216, entitled "Navigation Guidewire with Interlocked Coils," published Aug. 2, 2018, issued as U.S. Pat. No. 10,610,308 on Apr. 7, 2020, the disclosure of which is incorporated by reference herein; U. S. Pub. No. 2019/0192177, entitled "Reusable Navigation Guidewire," published Jun. 27, 2019, now abandoned, the disclosure of which is incorporated by reference herein; U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein in its entirety. In some such versions, guidewire module (12) includes an IGS navigation system, and connector (604) is operable to communicate position-indicative signals from the sensor of guidewire (602) to guidewire module (12).

In some versions, connector (604) is in the form of a slip coupling. Such a slip coupling may be configured to provide tensile strain relief for guidewire (602) while allowing guidewire (602) to freely rotate between connector (604) and any coupled components associated with guidewire module (12) (e.g., an additional cable coupled between connector (604) and guidewire module (12), etc.). This may prevent the build-up of torsion along any components that are proximal to connector (604) while guidewire (602) is rotated about the longitudinal axis of guidewire (602). In versions where guidewire (602) includes one or more optical fibers or other light-communicating features, connector (604) includes features allowing light to pass freely through connector (604), such that connector (604) maintains optical continuity between guidewire module (12) and guidewire (602). In versions where guidewire (602) includes one or more position sensors, connector (604) includes features that provide electrical continuity between guidewire module (12) and guidewire (602).

Figure 5:
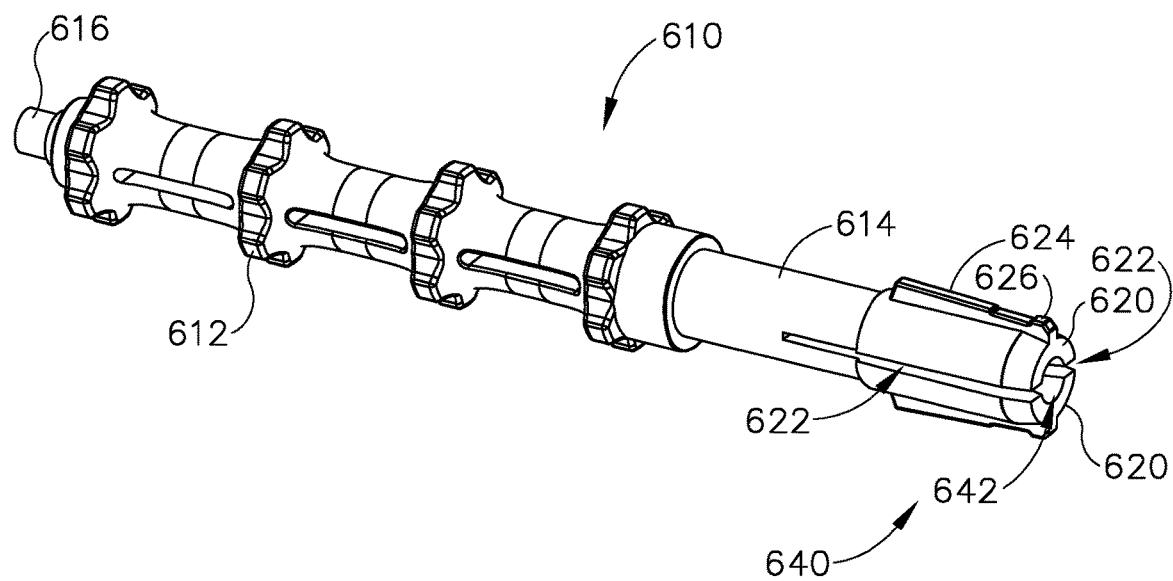
FIG. 5 depicts a perspective view of a spin actuator of the guidewire actuation assembly of FIG. 2.

As best seen in FIG. 5, spin actuator (610) of the present example includes a plurality of thumbwheel engagement features (612), a proximal shaft (614), and a distal shaft (616). Proximal shaft (614) includes a collet chuck feature (640) formed by a pair of collet leaves (620) that are separated by diametrically opposed longitudinally extending slots (622). Slots (622) are configured to provide clearance to allow collet leaves (620) to deflect inwardly toward each other to thereby grip guidewire (602). Each collet leaf (620) includes a fin (624) extending longitudinally and radially outwardly. Each fin (624) includes a proximally positioned detent feature (626).

Figure 4:
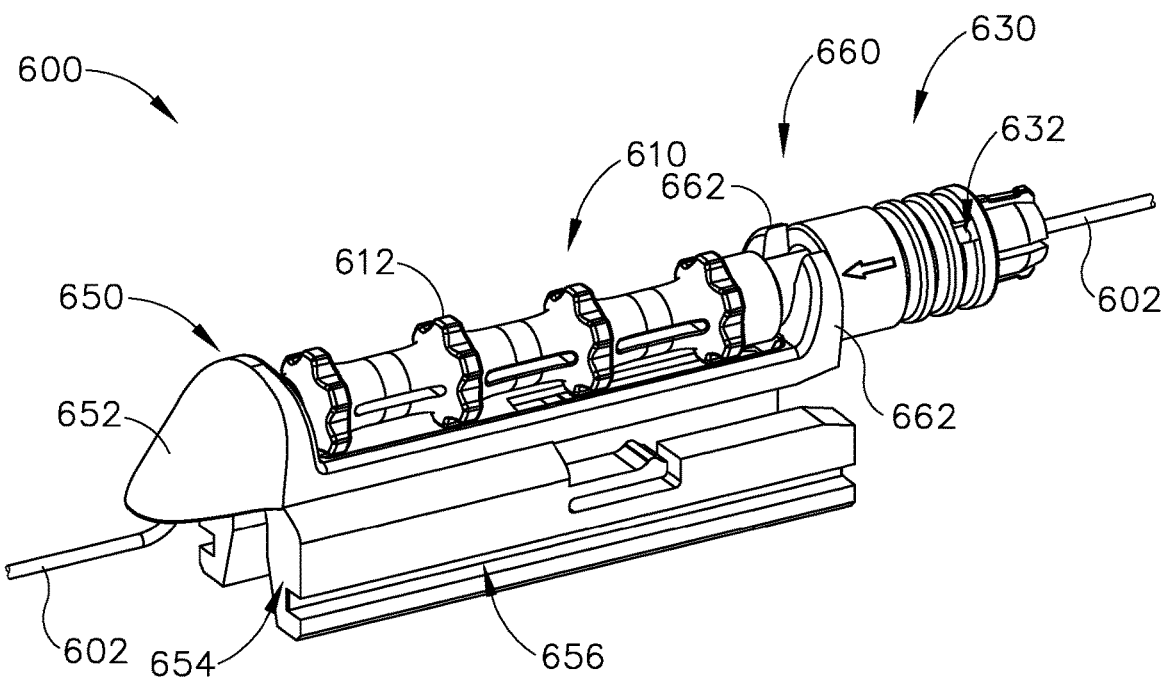
FIG. 4 depicts an enlarged perspective view of actuators of the guidewire actuation assembly of FIG. 2, with the collet collar of FIG. 3 in a distal position.

As shown in FIGS. 3-4, a collet collar (630) is configured to translate along proximal shaft (614) between a proximal position (FIG. 3) and a distal position (FIG. 4) to thereby transition collet chuck feature (640) between a locked state (FIG. 3) and an unlocked state (FIG. 4). The interior of collet collar (630) includes features that are operable to provide camming to drive leaves (620) inwardly toward each other as collet collar (630) is translated from the distal position to the proximal position. Detent features (626) of collet chuck feature (640) cooperate with notches (632) of collet collar (630) to selectively maintain the longitudinal position of collet collar (630) along proximal shaft (614) when collet collar (630) is in the proximal position. Detent features (626) thus cooperate with notches (632) to selectively maintain collet chuck feature (640) in the locked state.

When collet chuck feature (640) is in the locked state (FIG. 3), collet leaves (620) are deformed inwardly to grip guidewire (602) disposed in the central longitudinal bore (642) of spin actuator (610). When collet chuck feature (640) is in the unlocked state (FIG. 4), collet leaves (620) resiliently return to their natural position, thereby releasing their grip on guidewire (602). Thus, when collet chuck feature (640) is in the unlocked state, the operator may selectively adjust the longitudinal position of guidewire (602) relative to spin actuator (610). In some instances, the operator may wish to remove guidewire (602) from spin actuator (610) when collet chuck feature (640) is in the unlocked state. In some such instances, the operator may wish to exchange one guidewire (602) for another guidewire (602) (e.g., to exchange an illuminating guidewire (602) for a guidewire (602) having a position sensor, or vice-versa, etc.).

As best seen in FIGS. 3-4, slide actuator (650) of the present example comprises a distal nose portion (652), a lower base portion (654), and a proximal yoke (660). Distal nose portion (652) is configured to rotatably support distal shaft (615) of spin actuator (610). Proximal yoke (660) includes a pair of fork tines (662) that are configured to rotatably support proximal shaft (614) of spin actuator (610). Lower base portion (654) includes a pair of longitudinally extending recesses (656) that are configured to slidably receive corresponding rails (not shown) defined by housings (540) of handle assembly (500). Slide actuator (650) is operable to slide longitudinally relative to housings (540), to thereby translate guidewire (602) and spin actuator (610) longitudinally, while also allowing spin actuator (610) to rotate guidewire (602) relative to slide actuator (650). Distal nose portion (652) is also configured to redirect guidewire (602) from a first longitudinal axis (associated with the proximal portion of guidewire (602)) to a second longitudinal axis (associated with dilation catheter (702) (FIG. 1A) and the distal portion of guidewire (602)), with second longitudinal axis being parallel with the first longitudinal axis.

As noted above with reference to FIGS. 1A-1B, an operator may translate guidewire (602) longitudinally relative to handle assembly (500) by engaging guidewire actuation assembly (600) and sliding guidewire actuation assembly (600) longitudinally along handle assembly (500). Due to the position and configuration of guidewire actuation assembly (600), the operator may accomplish such motion by simply engaging guidewire actuation assembly (600) with the thumb (or another finger) of the hand that is grasping handle assembly (500). In some instances, the operator may also wish to rotate guidewire (602) about longitudinal axis of guidewire (602). This may be particularly desirable when distal end of guidewire (602) includes a preformed bend, as rotation of guidewire (602) may be used to advantageously reorient the bent distal end of guidewire (602) to thereby align the bent distal end of guidewire (602) with a targeted passageway. To provide such rotation, the operator may engage one or more thumbwheel engagement features (612) (FIG. 3) with the thumb (or another finger) of the hand that is grasping handle assembly (500). Guidewire actuation assembly (600) is thus configured to facilitate single-handed use including translation and rotation of guidewire (602). The elongate configuration of guidewire actuation assembly (600) may further facilitate single-handed use regardless of whether guidewire actuation assembly (600) is positioned distally or proximally along handle assembly (500).

II. EXEMPLARY GUIDEWIRE ACTUATION MECHANISM HAVING PLURALITY OF DISCRETE Locking Positions As described above, spin actuator (610) of guidewire actuation assembly (600) is transitioned between an unlocked state and a locked state relative to guidewire (602) by translating collet collar (630) proximally and distally over proximal shaft (614). In some instances, it may be desirable to integrate the locking features into the spin actuator (610) and to have a plurality of locking positions to facilitate the use of spin actuator (610) with guidewires (602), or other inserted instruments, with varying outer diameters. Integrating the locking features into the spin actuator (610) may also simplify manufacturing among other advantages. The following describes exemplary variations of spin actuator (610) that facilitate use with guidewires and other inserted instruments with various outer diameters, such that the variations of spin actuator (610) may readily accommodate and selectively lock relative to various instruments with various outer diameters.

Figure 6:
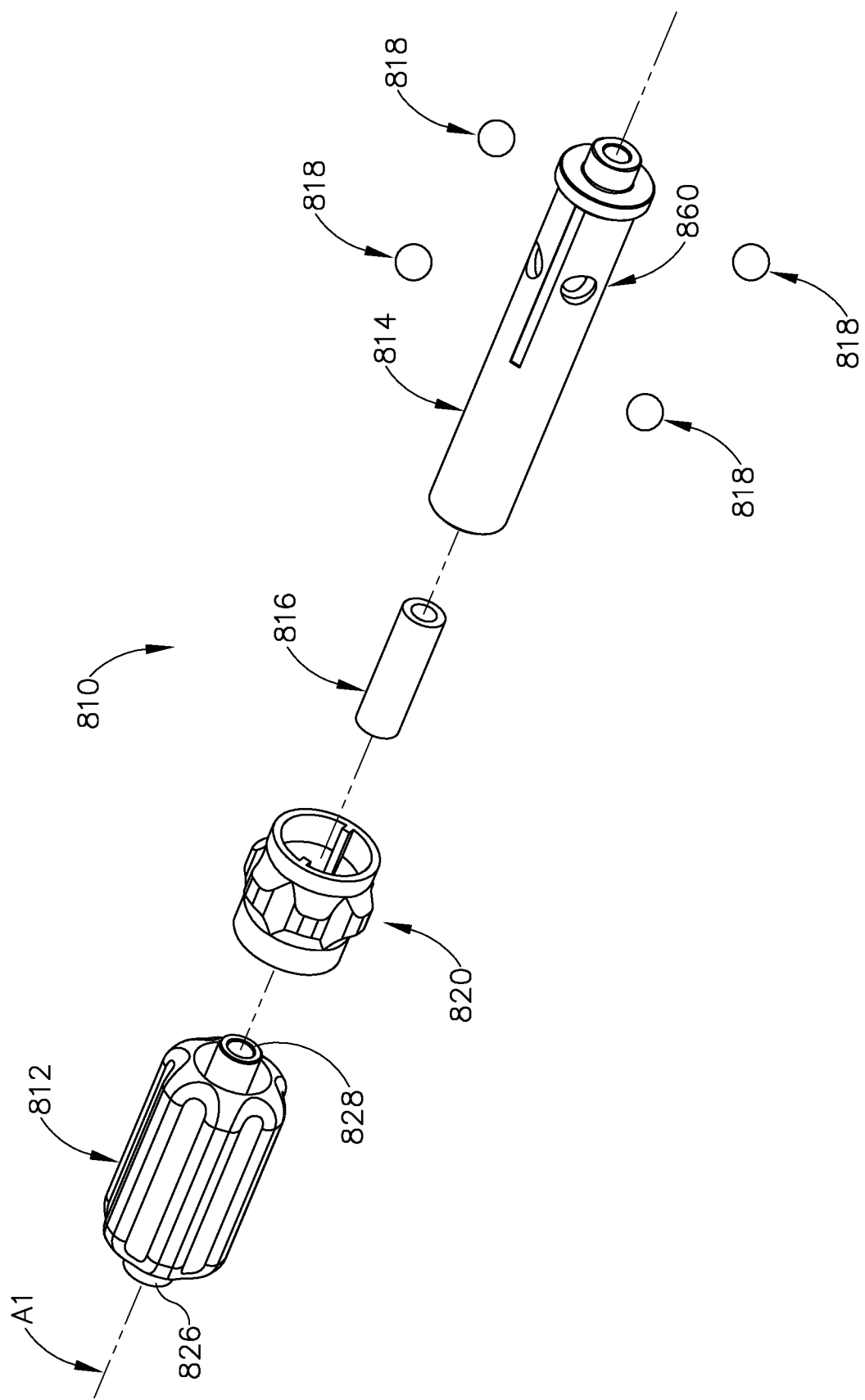
FIG. 6 depicts an exploded perspective view of an exemplary guidewire actuation mechanism for a guidewire actuation assembly that may be incorporated into the dilation instrument of FIG. 1A.

FIG. 6 shows an exemplary guidewire actuation mechanism (810) suitable for use with dilation instrument (10) (FIGS. 1A-1D) in place of spin actuator (610) (FIGS. 2-5) and collet collar (630) (FIGS. 2-4). Though not shown, it will be appreciated that guidewire actuation mechanism (810) may be incorporated within a guidewire actuation assembly (not shown) having a slidable support structure similar to slide actuator (650) (FIGS. 2-4) described above, to which guidewire actuation mechanism (810) is rotatably mounted, as described in greater detail below. As shown in FIG. 6, guidewire actuation mechanism (810) includes an engagement member (812), a hollow shaft (814), a resilient gripping member (816), a compression element (818), and a compression member (820). In the current example, compression element (818) is in the form of a ball. Alternatively, compression element (818) may take various other forms as will be apparent to those skilled in the art in view of the teachings herein.

Figure 12:
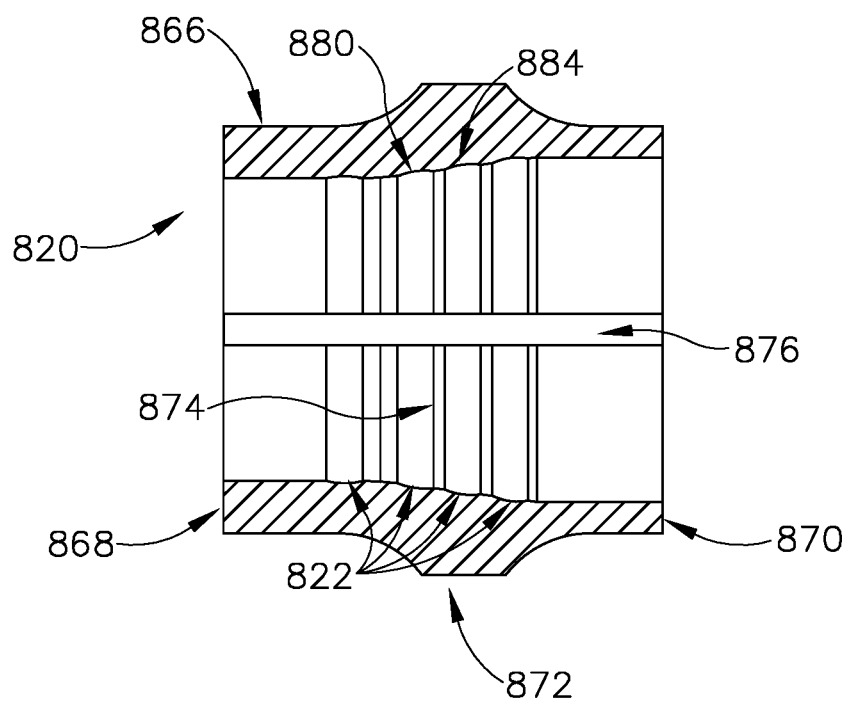
FIG. 12 depicts a cross-sectional view of the compression member of FIG. 11.

Guidewire actuation mechanism (810) is configured to lock and unlock upon various outer diameter elongate members (802, 803), as shown in FIGS. 17A-18B and described in greater detail below. In the present example, elongate member (802) is a guidewire, though other versions of elongate member (802) may include (but are not limited to) a dilation catheter, a suction instrument cannula, an endoscope, and/or various other kinds of elongate members as will be apparent to those skilled in the art in view of the teachings herein. Elongate member (802) translates along longitudinal axis (Al) through guidewire actuation mechanism (810) when guidewire actuation mechanism (810) is in an unlocked state (FIG. 17A). To reach the locked state, compression member (820) is translated distally in relation to engagement member (812). Compression member (820) urges compression element (818) radially inwardly against resilient gripping member (816), deforming resilient gripping member (816) radially inwardly to grip onto elongate member (802) (FIG. 17B), thereby locking elongate member (802). As shown in FIG. 12, compression member (820) has a conical inner surface (880) having a detent feature (822) to resist the compression member (820) from translating proximally and unlocking retain compression element (818) due to resilient gripping member (816) being biased to an expanded state. Detent features (822) also enable guidewire actuation mechanism (810) to lock upon different diameter elongate members (802, 803).

Figure 7:
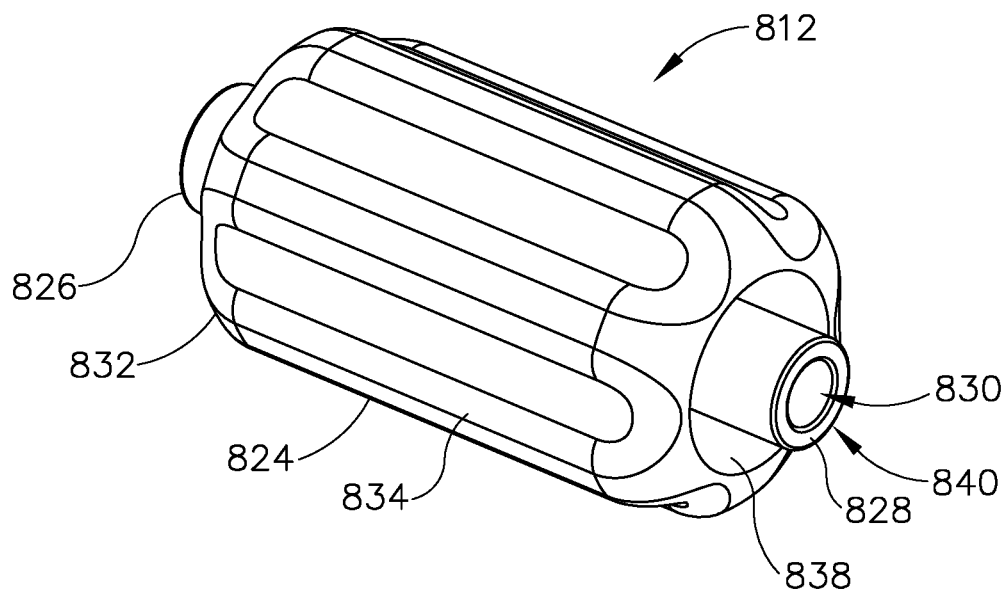
FIG. 7 depicts a perspective view of an engagement member of the guidewire actuation mechanism of FIG. 6.
Figure 8:
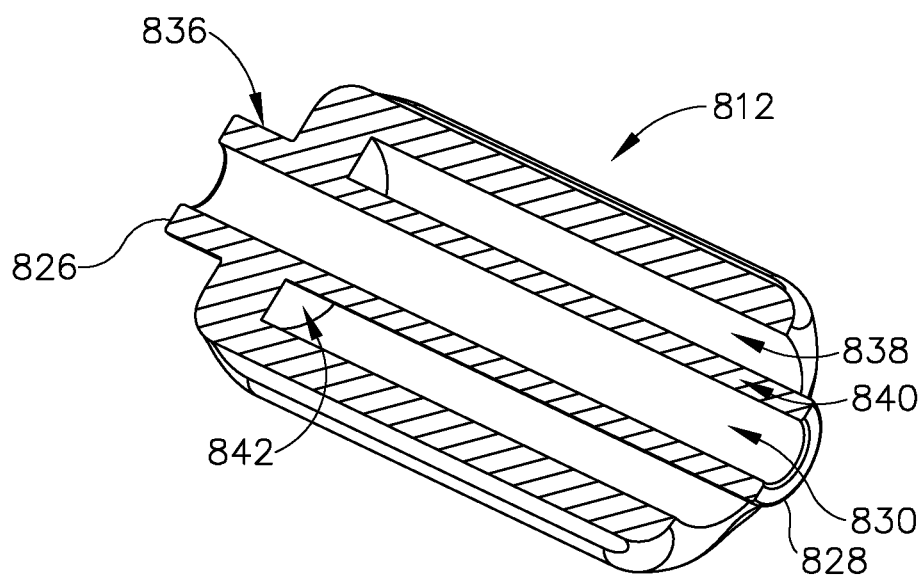
FIG. 8 depicts a cross-sectional view of the engagement member of FIG. 6.

As shown best in FIGS. 7-8, engagement member (812) of the present example includes a generally tubular body (824) having a proximal engagement member end (826), and a distal engagement member end (828). Tubular body (824) includes a first through bore (830) extending axially along longitudinal axis (A1) (FIG. 6). Tubular body (824) has a plurality of radially oriented finger engagement projections (832) angularly spaced apart from each other on an exterior of tubular body (834). Projections (832) are configured to be engaged by the operator. Tubular body (824) also has a proximal engagement member portion (836) proximate to proximal engagement member end (826). Proximate engagement member end (826) is configured to be rotatably supported by a first end portion of frame (660) (FIG. 4). Tubular body (824) has a first counterbore (838) extending proximally from distal engagement member end (828). First counterbore (838) has a diameter that is greater than first through bore (830). First counterbore and first through bore define a projection (840) extending distally from a base of first counterbore (842). Projection (840) is configured to prevent resilient gripping member (816) from moving proximally along longitudinal axis (A1) (FIG. 6).

Figure 9:
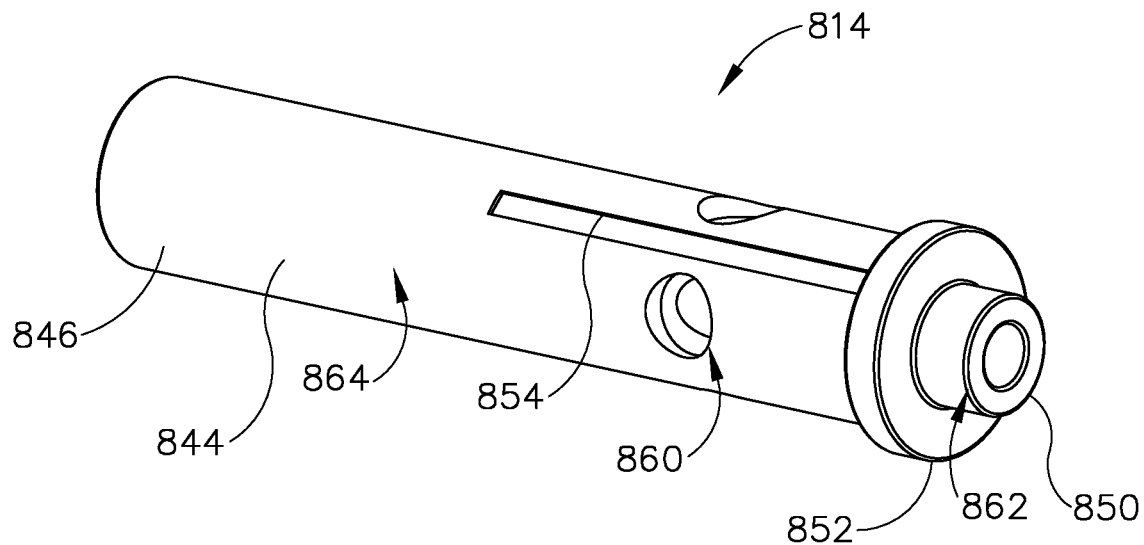
FIG. 9 depicts a perspective view of a hollow shaft of the guidewire actuation mechanism of FIG. 6.
Figure 10:
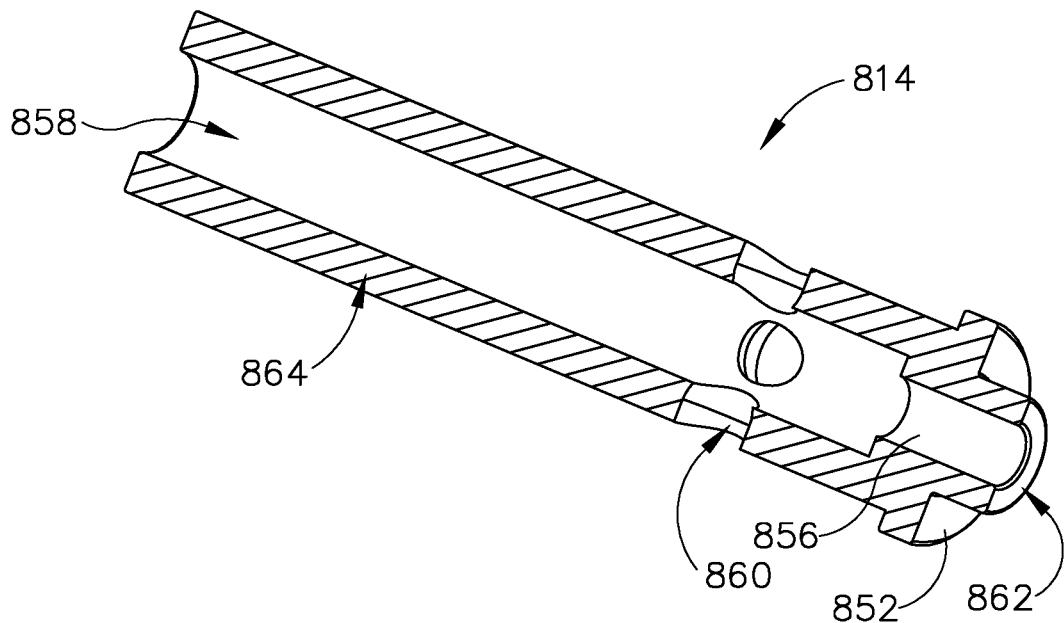
FIG. 10 depicts a cross-sectional view of the hollow shaft of FIG. 9.

FIGS. 9-10 show hollow shaft (814) of the present example including a generally tubular body (844), a proximal shaft end (846), and a distal shaft end (850). Tubular body (844) has an annular ring (852), a keyway (854), a second through bore (856), a second counterbore (858), an angularly spaced array of radial apertures (860), and a distal shaft portion (862). Each radial aperture (860) is radially deposed through tubular sidewall (864) of a distal shaft portion (862). Each radial aperture (860) is sized to accept a corresponding compression element (818) (FIG. 6). Distal shaft portion (852) is proximate to distal shaft end (850) and is configured to be rotatably supported by a second end portion of frame (652) (FIG. 4).

Annular ring (852) is located on a tubular sidewall of tubular body (844) proximate to distal shaft portion (862). Annular ring (852) locates guidewire actuation mechanism (810) linearly along longitudinal axis (A1). Keyway (854) extends distally in tubular sidewall (864) and terminates at annular ring (852). Second counterbore (858) extends distally from proximate shaft end (846) to a base of second counterbore (858). Second counterbore (858) is sized to accept resilient gripping member (816). Second through bore (856) extends from distally from base of second counterbore (858) to distal shaft end (850).

Figure 11:
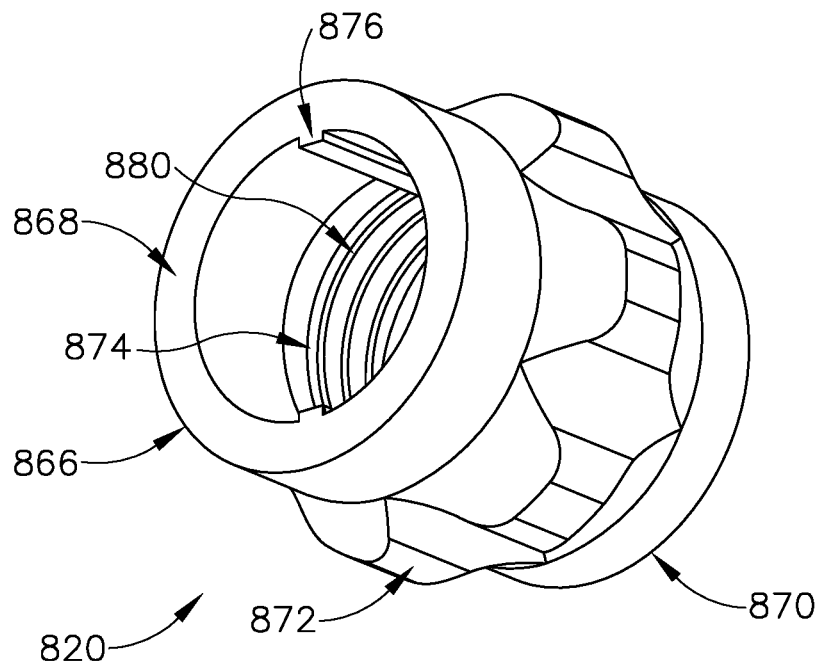
FIG. 11 depicts a perspective view of a compression member of the guidewire actuation mechanism of FIG. 6.

FIGS. 11-12 show compression member (820) of the present example having a generally annular body (866) having a proximal member end (868) and a distal member end (870). Annular body (866) has a plurality of radially extending finger engagement nubs (872) angularly spaced apart from each other on an exterior of annular body (866). Finger engagement nubs (872) are configured to be engaged by the operator. Compression member (820) is configured to be slidably disposed over hollow shaft (814) through a third through bore (874) extending distally from proximal member end (868) to distal member end (870). Third through bore (874) has a keyway projection (876) extending distally along longitudinal axis (A1). Keyway projection (876) is configured to slidably mate with keyway (854) (FIG. 9) of hollow shaft (814). Compression member (820) selectively translates longitudinally along hollow shaft (814) between a locked and unlocked position. In the present example, compression member (820) is in the form of a collar. Compression member (820) includes a conical inner surface (880) configured to engage compression elements (818). Conical inner surface (880) extends distally from proximal member end (868) to distal member end (870). Proximal member end (868) has a smaller inner diameter in relation to distal member end (870). Conical inner surface (880) has a plurality of detent features (822) linearly displaced along conical inner surface (880) and configured to retain compression member (820) in a plurality of locked positions. Each detent feature (822) has an arcuate radius (884) configured to retain different sized elongate members (802, 803) in the locked position by retaining compression elements (818) (FIG. 6). Compression element (818) in the present example are in the form of balls. Detent features (822) require the operator to apply additional longitudinal force to transition compression element (818) from the locked position to the unlocked position or vice-versa. This additional longitudinal force provides tactile feedback to the operator. This feedback aids the operator in distinguishing whether compression element (818) has been retained by detent feature (822). Additionally, the detent features (822) prevent compression member (820) from inadvertently slipping longitudinally, thereby helping maintain the locked state.

Figure 13:
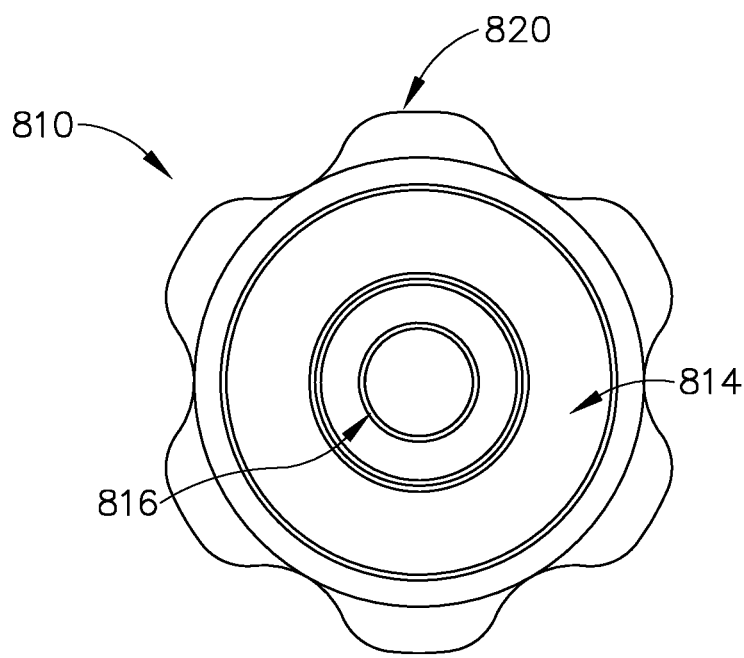
FIG. 13 depicts an end view from the distal end of the guidewire actuation mechanism of FIG. 6 in an unlocked state.
Figure 14:
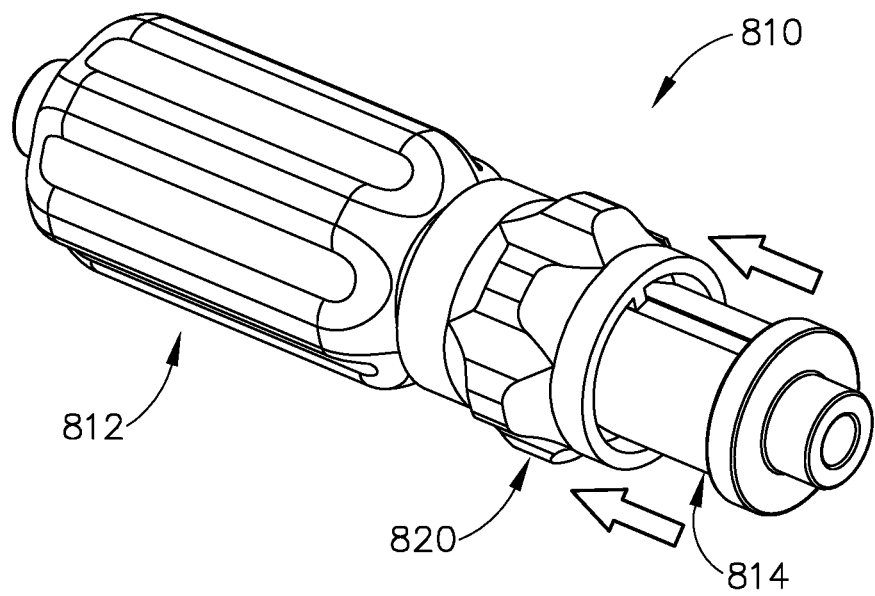
FIG. 14 depicts a perspective view of the guidewire actuation mechanism of FIG. 6 being transitioned into the unlocked state of FIG. 13.

FIGS. 13-14 show guidewire actuation mechanism (810) in the unlocked position. It is to be noted that in FIG. 13 resilient gripping member (816) in an expanded state. In the present example, guidewire actuation mechanism (810) is configured to accommodate elongate members (802, 803) (FIGS. 17-18) or other instruments having a diameter up to approximately 2.2 millimeters. This maximum diameter is governed by the diameter of resilient gripping member (816) (FIG. 6) through bore (888) (FIGS. 17A-B) when resilient gripping member (816) is in expanded state. Of course, 2.2 millimeters is just one merely illustrative example. Guidewire actuation mechanism (810) may alternatively be configured to accommodate elongate members (802, 803) (FIGS. 17A-18B) or other instruments up to any other suitable maximum diameter.

Figure 15:
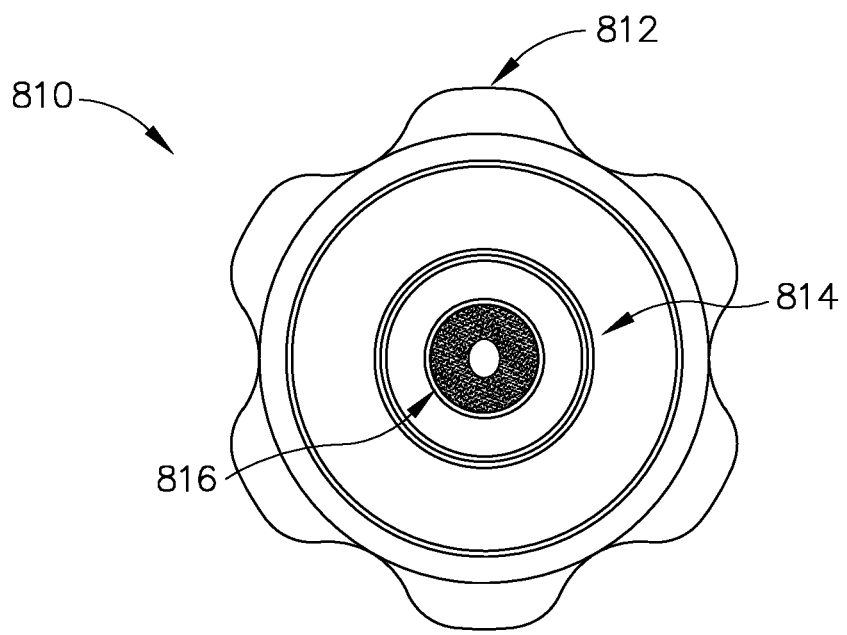
FIG. 15 depicts an end view from the distal end of the guidewire actuation mechanism of FIG. 6 in a locked state.
Figure 16:
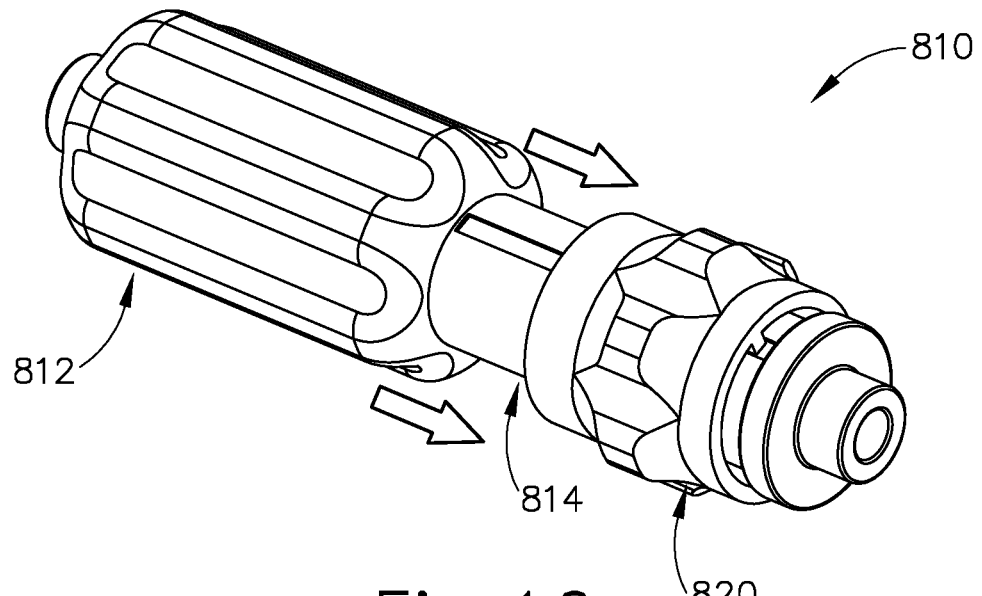
FIG. 16 depicts a prospective view of the guidewire actuation mechanism of FIG. 6 being transitioned into the locked state of FIG. 15.

FIG. 15-16 shows guidewire actuation mechanism (810) in the locked state. It is to be noted that resilient gripping member (816) is in a distorted state and resilient gripping member (816) is distorted towards longitudinal axis (A1). In the locked state the minimum diameter elongate member (802) that may be fitted is 0.75 millimeters. Minimum diameter is governed by resilient gripping member through bore (888) (when the resilient gripping member is in distorted state. Of course, 0.75 millimeters is just one merely illustrative example. Guidewire actuation mechanism (810) may alternatively be configured to accommodate elongate members (802, 803) or other instruments down to any other suitable minimum diameter.

FIG. 17A shows guidewire actuation mechanism (810) transitioning spin actuator (810) from the locked position to the unlocked position. Compression member (820) is translated proximally along the longitudinal axis (A1) to unlock elongate member (802). Resilient gripping member (816) is biased to restore resilient gripping member (816) to an expanded state. Resilient gripping member (816) in the expanded state has generally cylindrical configuration. Resilient gripping member (816) moves radially away from elongate member (802) and thereby permits translation of elongate member (802) through guidewire actuation mechanism (810) when guidewire actuation mechanism (810) is in the unlocked state. A gripping member through bore (888) conforms to the size of first and second through bores (830, 856) when resilient gripping member (816) in the unlocked position. In the unlocked state, resilient gripping member (816) is defined by second counterbore (858) of hollow shaft (814), gripping member through bore (888). Elongate member (802) may be freely translated through guidewire actuation mechanism (810).

FIG. 17B shows guidewire actuation mechanism (810) transitioning the spin actuator (810) from the unlocked position to the locked position. Compression member (820) is distally translated along longitudinal axis (A1) to the locked position. When compression member (820) is translated distally, conical inner surface (880) of compression member (820) urges compression elements (818) radially inwardly toward elongate member (802). Compression element (818) urges resilient gripping member (816) radially inwardly, elastically deforming resilient gripping member (816), causing resilient gripping member (816) to bear inwardly against elongate member (802), and locking elongate member (802) through friction. Detent features (822) on conical inner surface (880) hold compression elements (818) in the locked position on different sized elongate members (802, 803) (FIGS. 18A-18B).

FIGS. 18A-B shows guidewire actuation mechanism (810) fitted with a different elongate member (803) having a diameter that is larger than the diameter of elongate member (802). By way of example only, elongate member (802) may comprise a guidewire while elongate member (803) comprises a dilation catheter, suction cannula, endoscope, etc. In the example of FIGS. 18A-B, elongate member (803) is disposed in bores (830, 856, 874) of guidewire actuation mechanism (810). FIG. 18A shows guidewire actuation mechanism (810) transitioning from the locked position to the unlocked position. FIG. 18B shows guidewire actuation mechanism (810) transitioning from the unlocked position to the locked position.

In the locked position, compression members (820) distally translates along longitudinal axis (A1). When compression member (820) is translated distally conical inner surface (880) of compression member (820) urges compression elements (818) radially inwardly toward guidewire (802, 803). Compression element (818) urges resilient gripping member (816) radially inwardly, elastically deforming resilient gripping member (816) causing resilient gripping member (816) to bear inwardly against guidewire (802, 803) and lock guidewire (802, 803) through friction. Detent features (822) on conical inner surface (880) hold compression elements (818) in the locked position with different sized elongate members (802, 803). It should be noted that compression member (820) will not be distally translated as far as compression member (820) when a larger elongate member (803) is fitted. Therefore, on larger elongate member (803), compression elements (818) will engage more distally located detent feature (822) than when fitted with a smaller elongate member (802).

Figure 19:
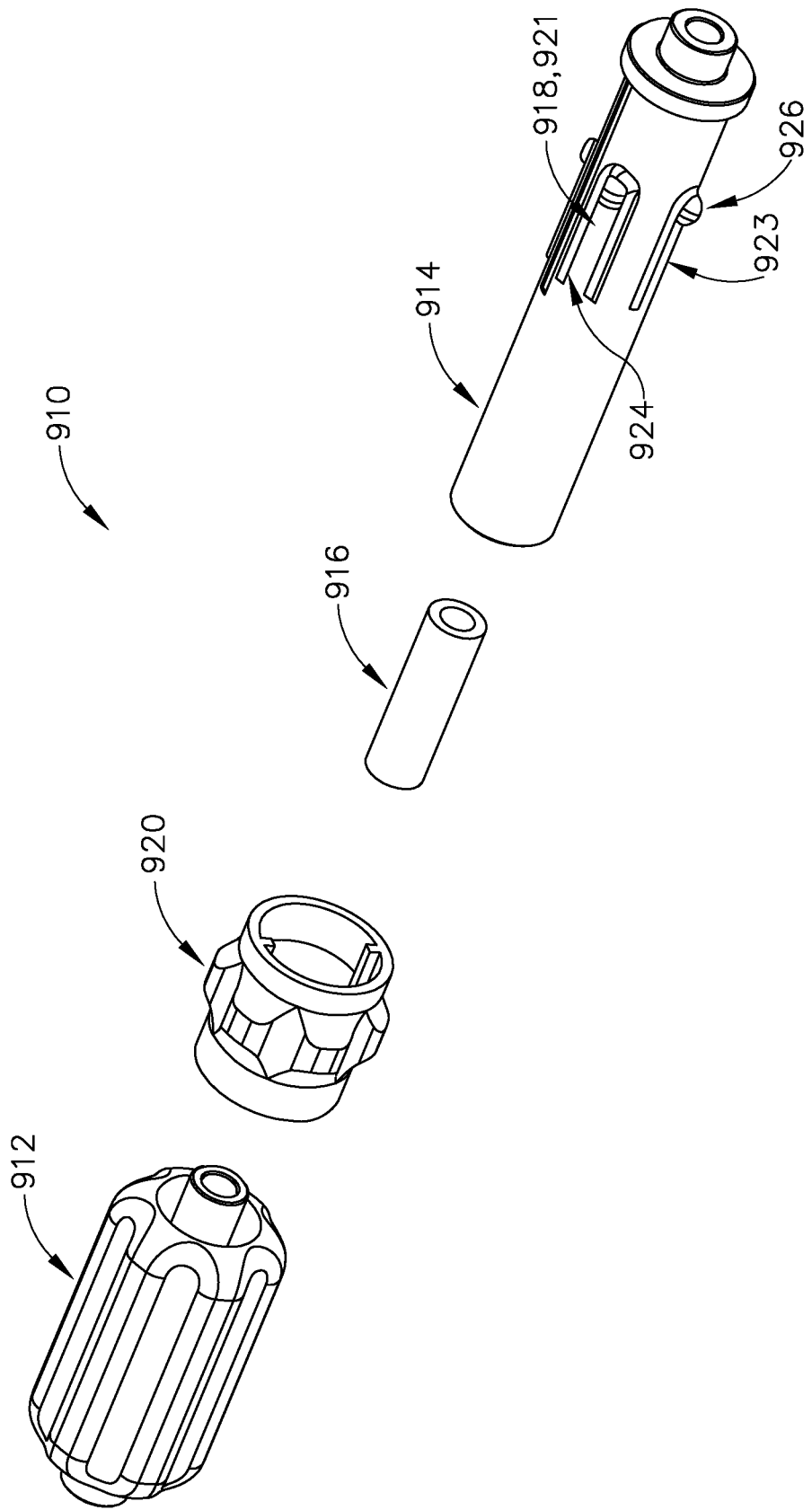
FIG. 19 depicts an exploded perspective view of another exemplary guidewire actuation mechanism for a variable diameter actuator assembly that may be incorporated into the dilation instrument of FIG. 1A.
Figure 20A:
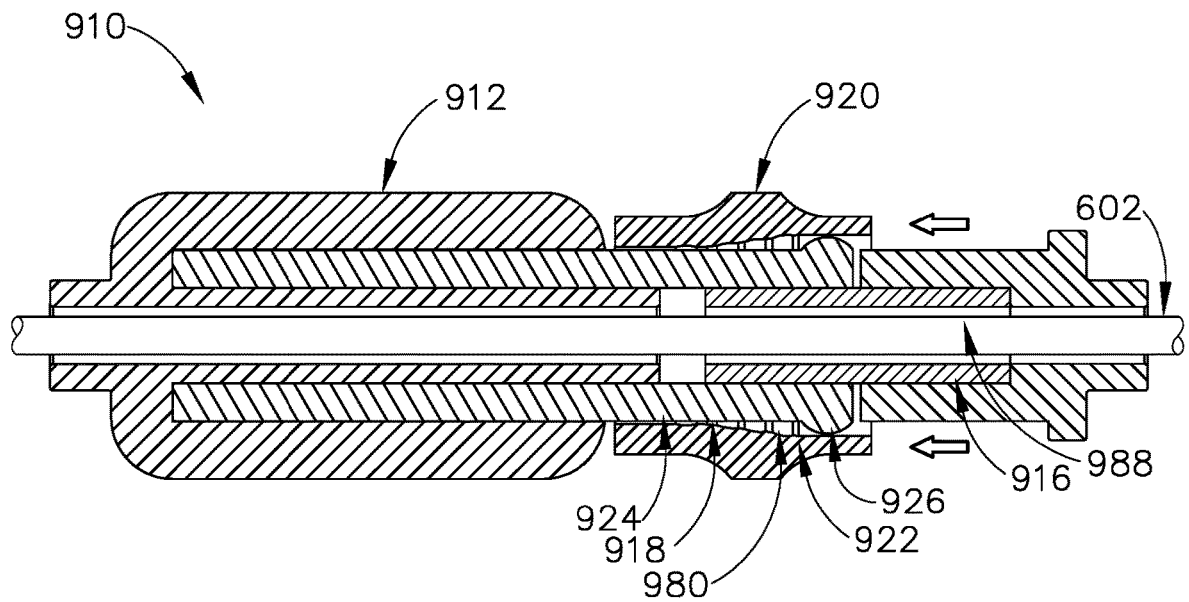
FIG. 20A depicts a cross-sectional view of the guidewire actuation mechanism of FIG. 19 in an unlocked state.
Figure 20B:
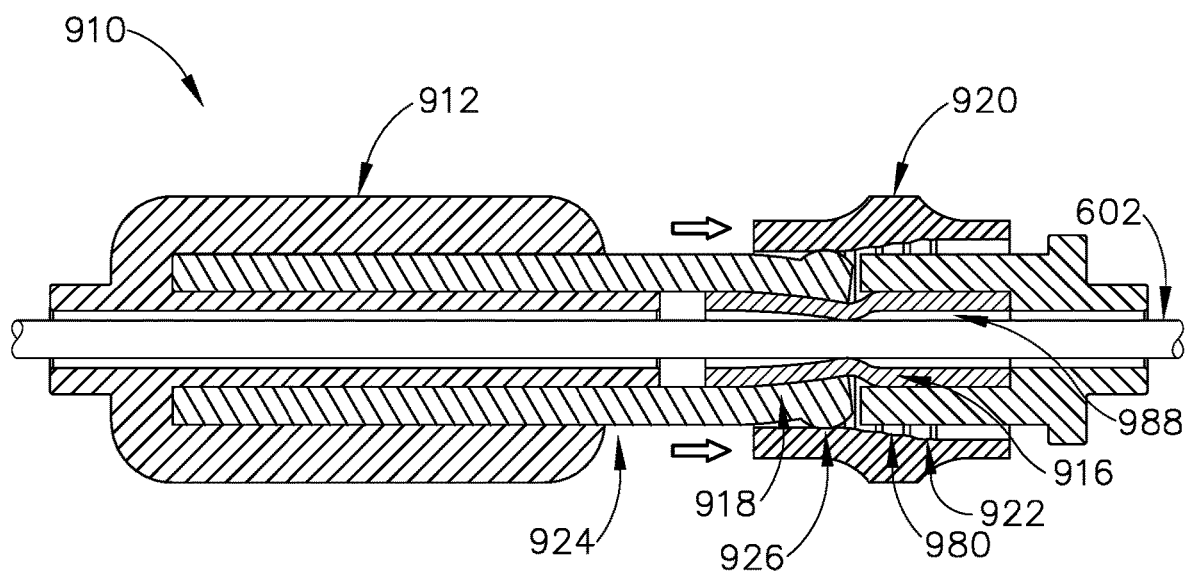
FIG. 20B depicts a cross-sectional view of the guidewire actuation mechanism of FIG. 19 in a locked state.
Figure 21:
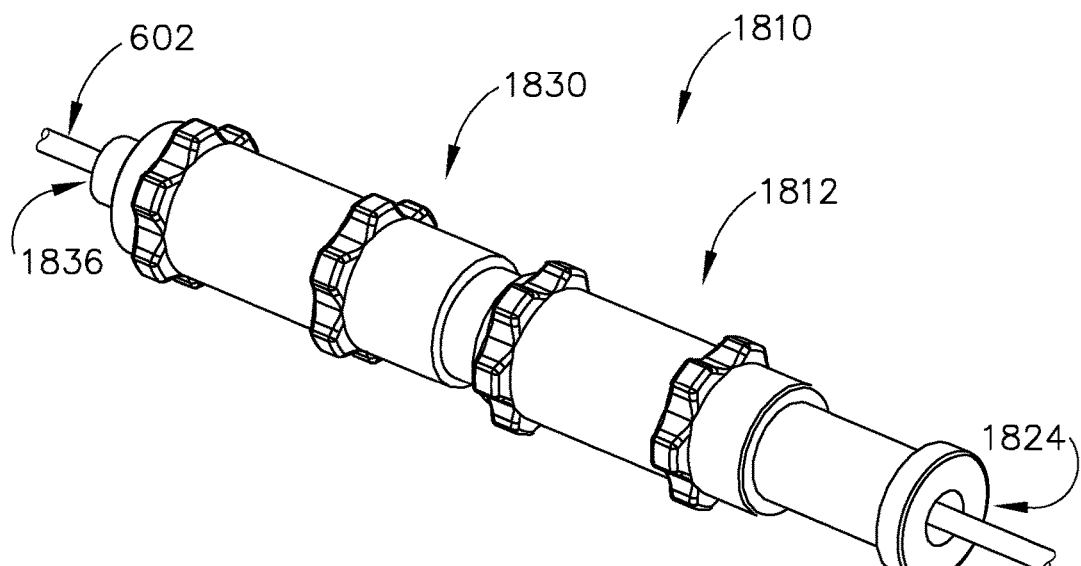
FIG. 21 depicts a perspective view of still another exemplary guidewire actuation mechanism that may be incorporated into the dilation instrument of FIG. 1A.

FIG. 19-20B show another example of a guidewire actuation mechanism (910) that is substantially similar to guidewire actuation mechanism (810) described above. In the present example, guidewire actuation mechanism (910) includes an engagement member (912), a hollow shaft (914), a resilient gripping member (916), a compression element (918), and a compression member (920). Guidewire actuation mechanism (910) is also configured to lock and unlock upon different diameter elongate members (802, 803). In the present example, hollow shaft (914) differs from hollow shaft (814) in that hollow shaft (914) has an integrated compression element (918) where compression element (818) is separate from hollow shaft (814). Hollow shaft (914) includes a plurality of compression elements (918) in the form of a flexible arm (921). Each flexible arm (921) has a flexible arm body (923) which extends distally from a base end of flexible arm (924) to an arcuate projection (926). The base end of each flexible arm (924) is integrally attached to hollow shaft (914). Each flexible arm (921) has an arcuate projection (926) located distally from base end of flexible arm (924). Each arcuate projection (926) is configured to engage conical inner surface (914) when compression member (920) is translated distally. Compression member (920) also has a conical inner surface (980) similar to conical inner surface (880). Conical inner surface (980) also has a plurality of detent features (922). Arcuate projections (926) are configured to be retained by plurality of detent features (922). Arcuate projections (926) perform similarly to compression elements (818). However, flexible arms (921), similar to resilient gripping member (916), are resiliently biased to an expanded state of rest.

FIG. 20A shows guidewire actuation mechanism (910) in the unlocked position. When in the unlocked position, flexible arms (921) resiliently return radially outwardly to straight configurations, and resilient gripping member (916) being biased to an expanded state. Resilient gripping member (916) in the expanded state has a larger diameter gripping member bore (988).

FIG. 20B shows guidewire actuation mechanism (910) in the locked position. When in the locked position, flexible arms (921) deform radially inwardly, engaging resilient gripping member (916) in response to being engaged by conical inner surface (980); and thereby deform resilient gripping member (916) to reduce the effective inner diameter of gripping member bore (988), thereby gripping elongate member (802).

While guidewire actuation mechanism (810, 910) have been described above as selectively gripping, rotating, and translating a guidewire (802, 803), it should be understood that guidewire actuation mechanism (810, 910) may alternatively be used to selectively grip, rotate, and translate virtually any flexible instrument. Merely illustrative examples of flexible instruments or other elongate members (802, 803) that may be used in combination with guidewire actuation mechanism in place of guidewire (602) include, but are not limited to, RF ablation catheters, balloon dilation catheters, biopsy instruments, and other flexible instruments. Other examples of flexible instruments or other elongate members (802, 803) that may be used in combination with guidewire actuation mechanism (810, 910) in place of guidewire (602) will be apparent to those skilled in the art in view of the teachings herein.

III. EXEMPLARY GUIDEWIRE ACTUATION MECHANISM HAVING THREADEDLY LOCKING MEMBERS

FIGS. 21-27B show still another example of guidewire actuation mechanism (1810) that is substantially similar to guidewire actuation mechanism (910) discussed above except as otherwise explicitly noted herein. Like guidewire actuation mechanism (910), guidewire actuation mechanism (1810) is suitable for use with dilation instrument (10) (FIGS. 1A-1D) in place of spin actuator (610) (FIGS. 2-5) and collet collar (630) (FIGS. 2-4). Though not shown, it will be appreciated that spin actuator (1810) may be incorporated within a guidewire actuation assembly (not shown) having a slidable support structure similar to slide actuator (650) (FIGS. 2-4) described above, to which guidewire actuation mechanism (1810) is rotatably mounted.

As described above, guidewire actuation mechanism (910) fixes elongate member (802) relative to guidewire actuation mechanism (910) by translating compression member (920) longitudinally, which causes resilient gripping member to frictionally engage elongate member (802). Guidewire actuation mechanism (1810), like guidewire actuation mechanism (910), is also configured to fix elongate member (802) relative to guidewire actuation mechanism (810). However, unlike guidewire actuation mechanism (910), which utilizes longitudinal movement to fix elongate member (802), guidewire actuation mechanism (1810) of this example fixes elongate member (802) by utilizing rotational movement about a longitudinal axis (A1), as described in greater detail below.

Guidewire actuation mechanism (1810) includes a first coupling member (1812), a second coupling member (1830), and a compressible body (1840) arranged between confronting ends of first and second coupling members (1812, 1830) along a longitudinal axis (A1) of assembly (1810). As described in greater detail below, first and second coupling members (1812, 1830) are configured to threadedly couple together via relative rotation about longitudinal axis (A1) to compress compressible body (1840) radially inwardly to frictionally engage elongate member (802). Upon reaching a sufficiently compressed state in response to relative rotation between coupling members (1812, 1830), compressible body (1840) fixes elongate member (802) axially and rotationally relative to guidewire actuation mechanism (1810).

Figure 22:
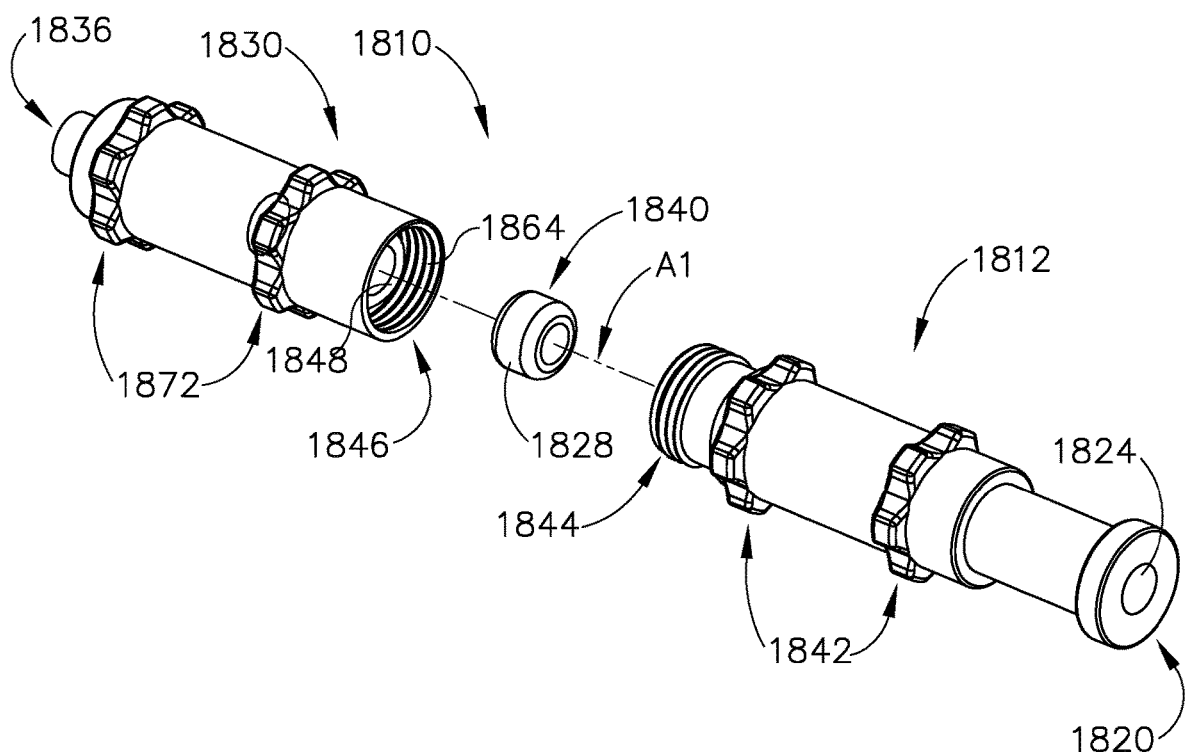
FIG. 22 depicts an exploded perspective view of the guidewire actuation mechanism of FIG. 21.
Figure 23:
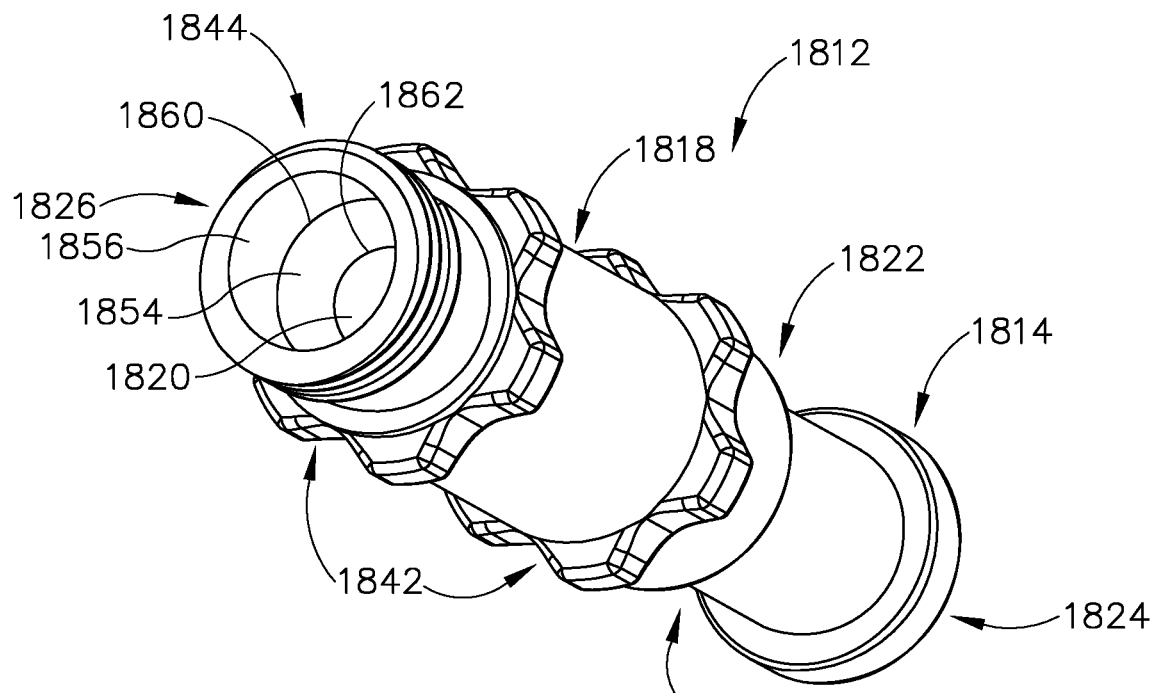
FIG. 23 depicts a perspective view of a first member of the guidewire actuation mechanism of FIG. 21.
Figure 24:
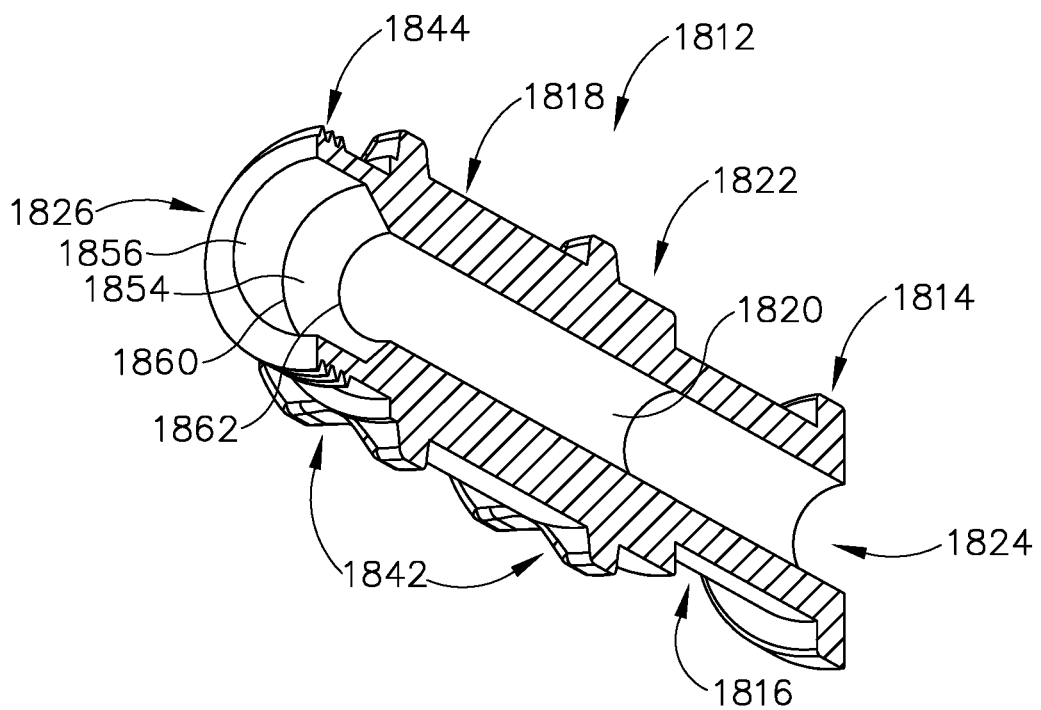
FIG. 24 depicts a cross-sectional view of the first member of FIG. 23.

As shown best in FIGS. 23-24, first coupling member (1812) of the present example includes a generally tubular body (1822) having a proximal end (1824), a distal end (1826), and a first through bore (1820) that extends along longitudinal axis (A1) (FIG. 22) between proximal and distal ends (1824, 1826). Tubular body (1822) of first coupling member (1812) includes a collar (1814) arranged at proximal end (1824), a first proximal shaft portion (1816) extending distally from collar (1814), and a first distal shaft portion (1818) extending distally from first proximal shaft portion (1816). First distal shaft portion (1818) has a plurality of finger engagement projections (1842) arranged radially on the exterior of first distal shaft portion (1818), and which are configured to be engaged by a user. Distal end (1826) of first coupling member (1812) includes a first threaded portion (1844) configured to threadedly engage a second threaded portion (1846) (FIG. 25) of second coupling member (1830) (FIGS. 25-27B), as described in greater detail below. In the present version, first threaded portion (1844) includes external right-hand threads. However, it will be appreciated that first threaded portion (1844) may include left-hand threads and/or internal threads in other versions, provided that first threaded portion (1844) is configured to threadedly engage second threaded portion (1846). In some other variations, coupling members (1812, 1830) are coupled together via a bayonet fitting instead of via threaded portions (1844, 1846). Various suitable ways in which threaded portions (1844, 1846) may be substituted with complementary bayonet fitting portions will be apparent to those skilled in the art in view of the teachings herein.

Distal end (1826) of first coupling member (1812) defines a first counterbore (1856) in communication with first through bore (1820). First counterbore (1856) has a diameter that is larger than a diameter of first through bore (1820). A conical shaped surface (1854) is positioned at a proximal end of first counterbore (1856) and tapers proximally from a larger first diameter (1860) to a smaller second diameter (1862). As described in greater detail below, conical shaped surface (1854) is configured to cooperate with a cylindrical projection (1864) (FIG. 25) of second coupling member (1830) (FIGS. 25-27B) to axially compress compressible body (1840) therebetween and thereby deform the compressible body radially inwardly against elongate member (802) (FIG. 27B).

Figure 25:
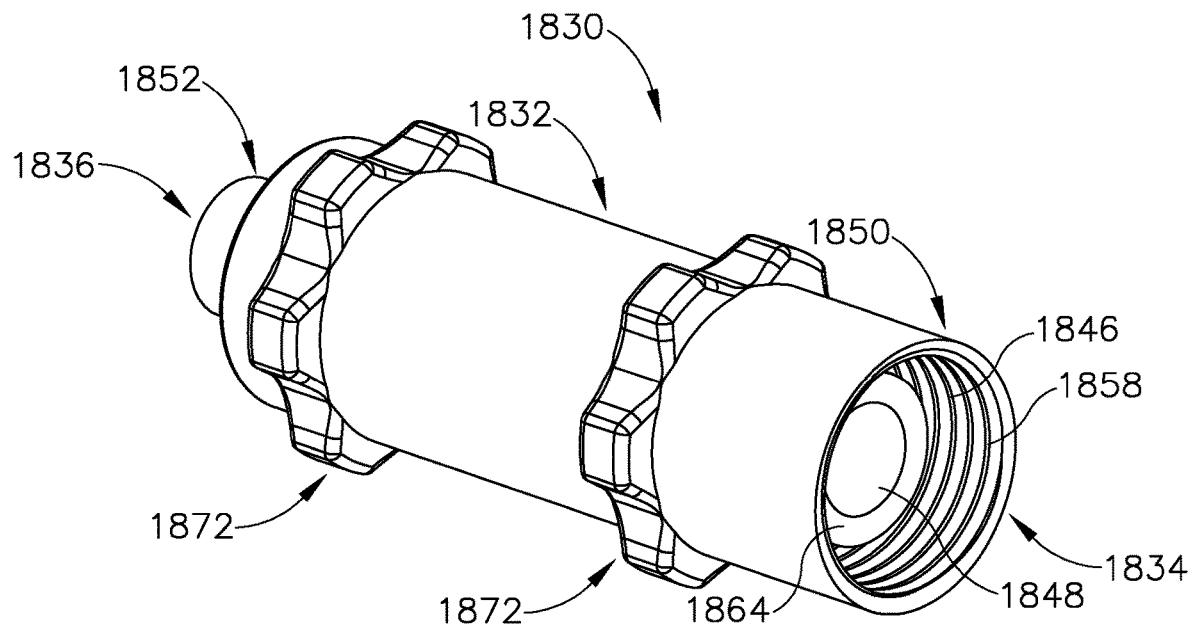
FIG. 25 depicts a perspective view of a second member of the guidewire actuation mechanism of FIG. 21.
Figure 26:
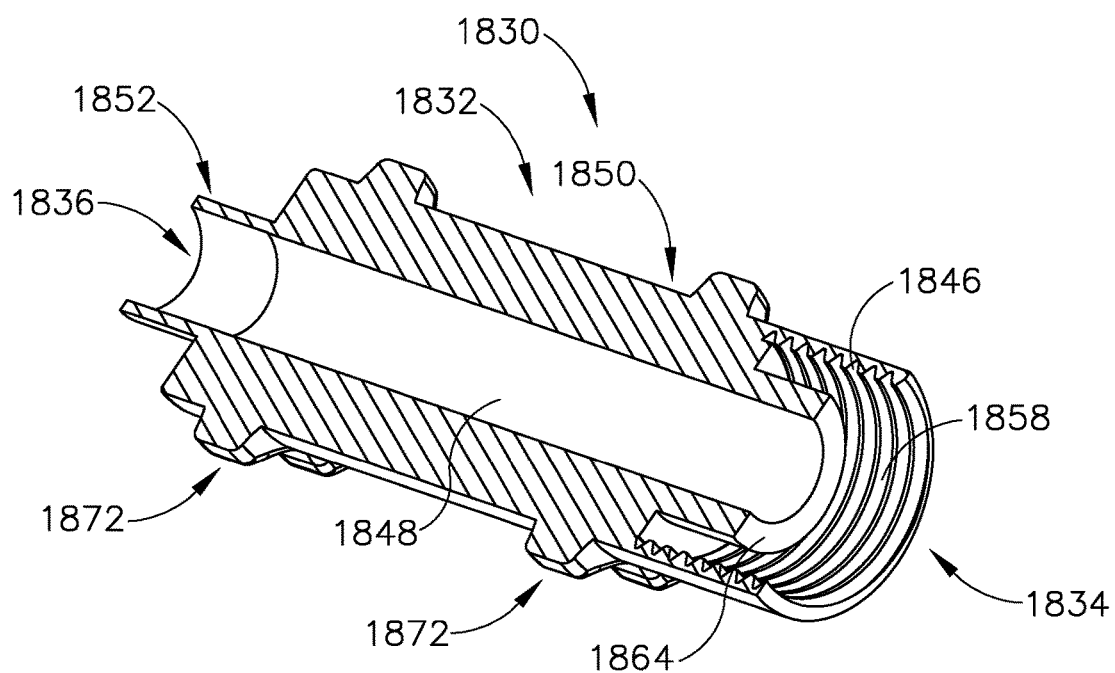
FIG. 26 depicts a cross-sectional view of the second member FIG. 25.

As shown best in FIGS. 25-26, second coupling member (1830) of the present example includes a generally tubular body (1832) having a proximal end (1834), a distal end (1836), and a second through bore (1848) extending axially along longitudinal axis (A1) (FIG. 22) between proximal and distal ends (1834, 1836). Second coupling member (1830) includes a second proximal shaft portion (1850) and a second distal shaft portion (1852). Second proximal shaft portion (1850) is larger in diameter relative to second distal shaft portion (1852). Second proximal shaft portion (1850) has a plurality of finger engagement projections (1872) arranged radially on the exterior of second proximal shaft portion (1850), and which are configured to be engaged by a user. Proximal end (1834) of second coupling member (1830) further includes a second counterbore (1858). An inner wall defining second counterbore (1858) has a second threaded portion (1846) configured to threadedly engage first threaded portion (1844) of first coupling member (1812) when coupling members (1812, 1830) are rotated relative to one another. In the present version, second threaded portion (1846) includes internal right-hand threads. However, it will be appreciated that second threaded portion (1846) may include left-hand threads and/or right-hand internal threads in other versions, provided that second threaded portion (1846) is configured to threadedly engage first threaded portion (1844). Proximal end (1834) of second coupling member (1812) further includes a cylindrical projection (1864) extending proximally from a distal base surface of second counterbore (1858), and which defines a proximal end of second through bore (1848).

As shown best in FIG. 22, compressible body (1840) of the present example has a generally annular shape. Additionally, compressible body (1840) may be composed of an elastomeric material that enables it to resiliently transition between a radially expanded, uncompressed state and a radially compressed state, such as a rubber or rubber-like material. As shown in FIGS. 27A and 27B, compressible body (1840) is positioned in first counterbore (1856) of first coupling member (1812), against conical shaped surface (1854). Compressible body (1840) of the present example defines a bore (1828) configured to coaxially align along longitudinal axis (A1) with first through bore (1820) and second through bore (1848) to receive elongate member (802) axially through bore (1828) of compressible body (1840).

As shown in FIG. 27A, compressible body (1840) is resiliently biased towards the radially expanded state in which elongate member (802) is freely translatable through first coupling member (1812), second coupling member (1830), and compressible body (1840). As shown in FIG. 27B, compressible body (1840) is configured to compress radially inwardly in response to relative rotation between first and second coupling members (1812, 1830) so that bore (1828) closes around elongate member (802). As described below, this radial compression causes compressible body (1840) to frictionally engage elongate member (802) and thereby fix elongate member (802) axially and rotationally relative to first and second coupling members (1812, 1830).

FIG. 27A shows guidewire actuation mechanism (1810) in an exemplary unlocked state in which first threaded portion (1844) of first coupling member (1812) is at least partially de-threaded from second threaded portion (1846) of second coupling member (1830). In the unlocked state, the compressible body (1840) is in the uncompressed state such that bore (1828) is enlarged about elongate member (802), thereby permitting elongate member (802) to freely translate axially through guidewire actuation mechanism (1810). While FIG. 27A shows an axial gap between compressible body (1840) and conical shaped surface (1854) when guidewire actuator assembly (1810) is in the unlocked state, it will be appreciated that compressible body (1840) may be in positioned in direct contact with conical shaped surface (1854) while remaining uncompressed.

FIG. 27B shows guidewire actuation mechanism (1810) in a locked state in which first and second coupling members (1812, 1830) have compressed compressible body (1840) axially so that compressible body (1872) has elastically deformed radially inwardly to frictionally engage (or "grip") elongate member (802). Transitioning guidewire actuation mechanism (1810) from the unlocked state shown in FIG. 27A to the locked state shown in FIG. 27B is achieved by providing relative rotation between first and second coupling members (1812, 1830) so that first and second threaded portions (1844, 1846) fully engage and drive coupling members (1812, 1830) axially toward one another. In response to this threaded engagement of first and second threaded portions (1844, 1846), cylindrical projection (1864) of second coupling member (1830) compresses compressible body (1840) axially against conical shaped surface (1854) of first coupling member (1812). As cylindrical projection (1864) advances closer to conical shaped surface (1854), conical shaped surface (1854) exerts a progressively increasing inward radial force on the outer diameter of compressible body (1840), thus causing compressible body (1840) to deform radially inwardly about elongate member (802). Continued threaded engagement of coupling members (1812, 1830) with one another causes compressible body (1840) to compress radially inwardly to the point that it frictionally engages and thereby fixes elongate member (802) axially and rotationally relative to first and second coupling members (1812, 1830).

It will be appreciated that guidewire actuation assembly (1810) may be returned to the unlocked state from the locked state by rotationally dethreading first and second coupling members (1812, 1830) from each other. As used herein, the term "dethreading" should not be read as requiring coupling members (1812, 1830) to be completely decoupled from each other. Instead, the term should be read to include the transition from the state shown in FIG. 27B to the state shown in FIG. 27A, where coupling members (1812, 1830) remain coupled together yet no longer cooperate to compress compressible body (1840) onto elongate member (802).

The relative rotation between first and second coupling members (1812, 1830) for transitioning between the unlocked state (FIG. 27A) and the locked state (FIG. 27B) can be achieved by rotating one coupling member (1812, 1830) while the opposing coupling member (1812, 1830) remains stationary. In other versions, both coupling members (1812, 1830) can be rotated relative to one another, in opposite directions. In either case, it will be understood that guidewire actuation assembly (1810) is suitably mounted to a support structure, which may be similar to slide actuator (650) (FIGS. 2-5) as described above, such that both coupling members (1812, 1830) are rotatable relative to the support structure, and such that at least one of coupling members (1812, 1830) is translatable relative to the support structure. Such a configuration permits rotation of coupling members (1812, 1830) relative to one another and relative to the support structure, as well as axial advancement and separation of coupling members (1812, 1830) during rotational threading and dethreading of threaded portions (1844, 1846) as described above. In some versions, first coupling member (1812) may be rotatably and translatably mounted to a first end portion of the support structure (not shown) along first proximal shaft portion (1816), and second coupling member (1830) may be rotatably mounted to a second end portion of the support structure (not shown) at second distal shaft portion (1852).

As described above, compressible body (1840) of the exemplary version shown is compressed between a cylindrical projection (1864) and a conical shaped surface (1854). In other versions, various other suitable structures readily apparent to those of ordinary skill in the art may be implemented to compress compressible body (1840). For instance, first and second coupling members (1812, 1830) may include two opposed projections (1864), or two opposed conical shaped surfaces (1854).

While guidewire actuation mechanism (1810) has been described above as selectively gripping, rotating, and translating an elongate member (802), it should be understood that guidewire actuation mechanism (1810) may alternatively be used to selectively grip, rotate, and translate virtually any flexible instrument. Merely illustrative examples of flexible instruments or other elongate members (802, 803) that may be used in combination with guidewire actuation mechanism (1810) in place of guidewire (602) include, but are not limited to, RF ablation catheters, balloon dilation catheters, biopsy instruments, and other flexible instruments. Other examples of flexible instruments or other elongate members (802, 803) that may be used in combination with guidewire actuation mechanism (1810) in place of guidewire (602) will be apparent to those skilled in the art in view of the teachings herein.

IV. EXEMPLARY GUIDEWIRE ACTUATION MECHANISM HAVING SELECTIVE GRIPPING FEATURE

Figure 28:
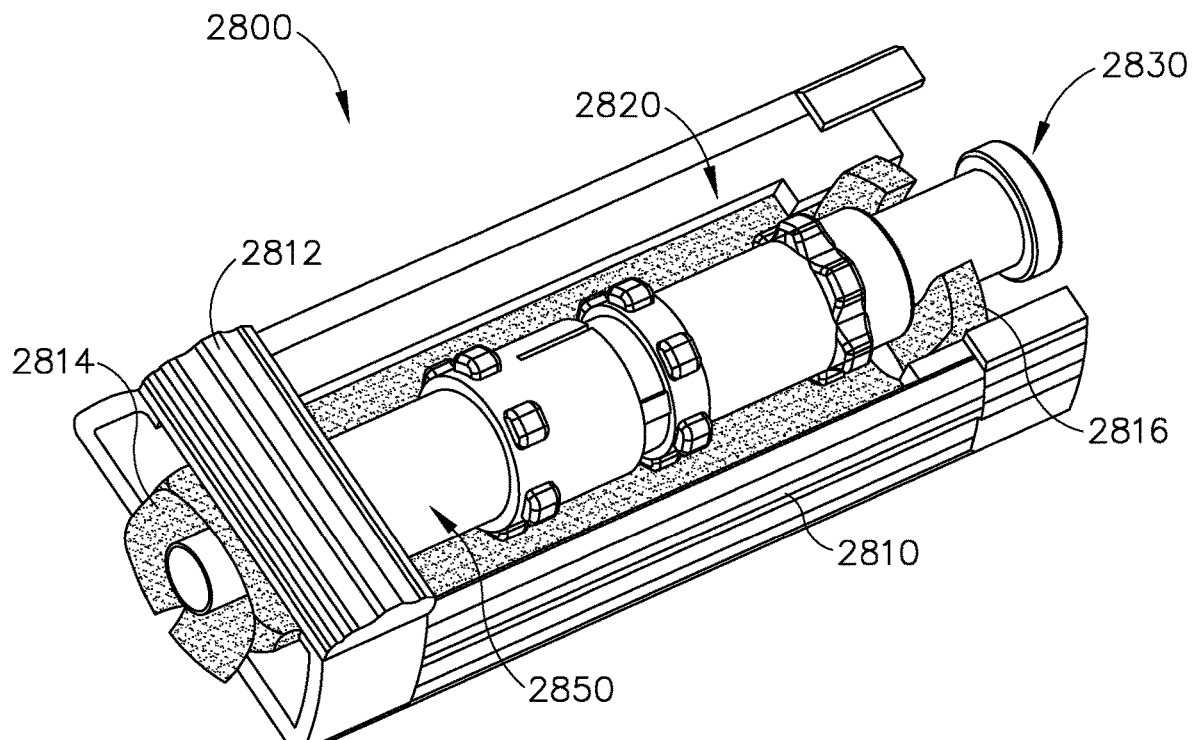
FIG. 28 depicts a perspective view of yet another exemplary guidewire actuation mechanism, incorporated into a guidewire actuation assembly that may be incorporated into the dilation instrument of FIG. 1A.

FIG. 28 shows yet another exemplary alternative guidewire actuation mechanism (2820) fitted within a guidewire actuation assembly (2800). This exemplary alternative guidewire actuation mechanism (2820) is substantially similar to guidewire actuation mechanism (1810) (FIGS. 21-22) discussed above except as otherwise explicitly noted herein. Like guidewire actuation mechanism (1810) (FIGS. 21-22), guidewire actuation mechanism (2800) may be incorporated into dilation instrument (10) (FIG. 1A-1D) in place of spin actuator (610) (FIGS. 2-5) and collet collar (630) (FIG. 2-4). Both guidewire actuation mechanism (1810) and guidewire actuation mechanism (2820) have a resilient member (1840, 2820) that grips elongate member (802). Guidewire actuation mechanism (1810) grips elongate member (802) by exerting force on compressible body (1840). In contrast, guidewire actuation mechanism (2820) of the present example grips elongate member (802) by releasing force on a gripping member (2860), discussed further below.

Guidewire actuation assembly (2800) of this example comprises a slide actuator (2810) and a guidewire actuation mechanism (2820). Slide actuator (2810) is configured to slidably couple with handle assembly (500) and thereby translate elongate member (802) longitudinally relative to handle assembly (500). Guidewire actuation mechanism (2820) is operable to selectively grip elongate member (802) and rotate elongate member (802) about the longitudinal axis of elongate member (802).

Slide actuator (2810) of the present example includes a grip feature (2812), a first yoke (2814), and a second yoke (2816). In some versions, grip feature (2812) and first yoke (2814) are at the distal end of guidewire actuation assembly (2800) while second yoke (2816) is at the proximal end of guidewire actuation assembly (2800). In some other versions, grip feature (2812), and first yoke (2814) are at the proximal end of guidewire actuation assembly (2800) while second yoke (2816) is at the distal end of guidewire actuation assembly (2800). Slide actuator (2810) is slidably coupled with handle assembly (500) and is thereby operable to translate guidewire actuation mechanism (2820) and elongate member (802) longitudinally relative to handle assembly (500). Grip feature (2812) is configured to facilitate engagement between an operator's thumb or finger and slide actuator (2810).

Figure 29:
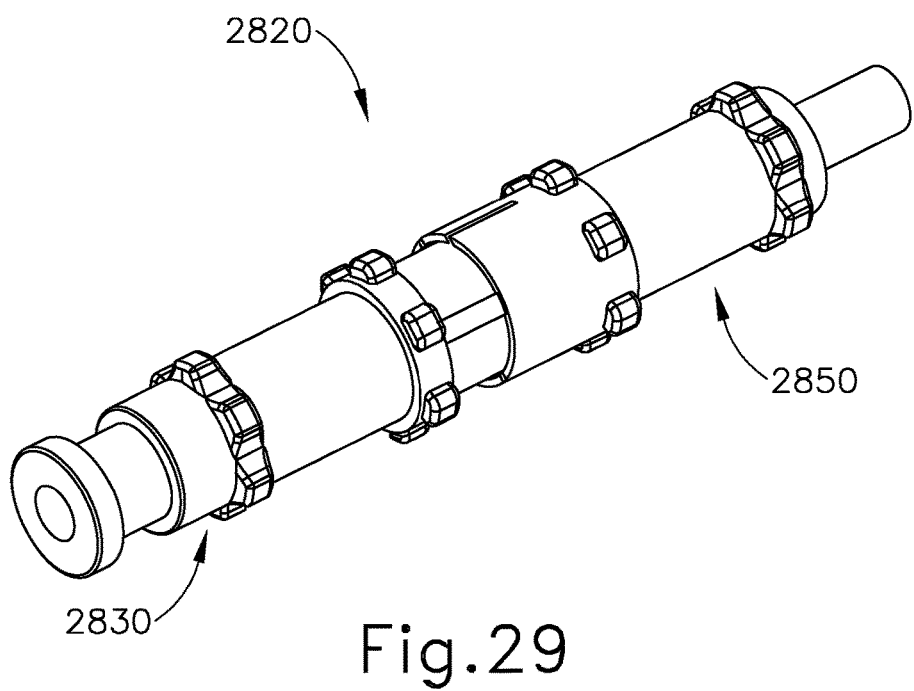
FIG. 29 depicts a perspective view of the guidewire actuation mechanism of the guidewire actuation assembly of FIG. 28.
Figure 30:
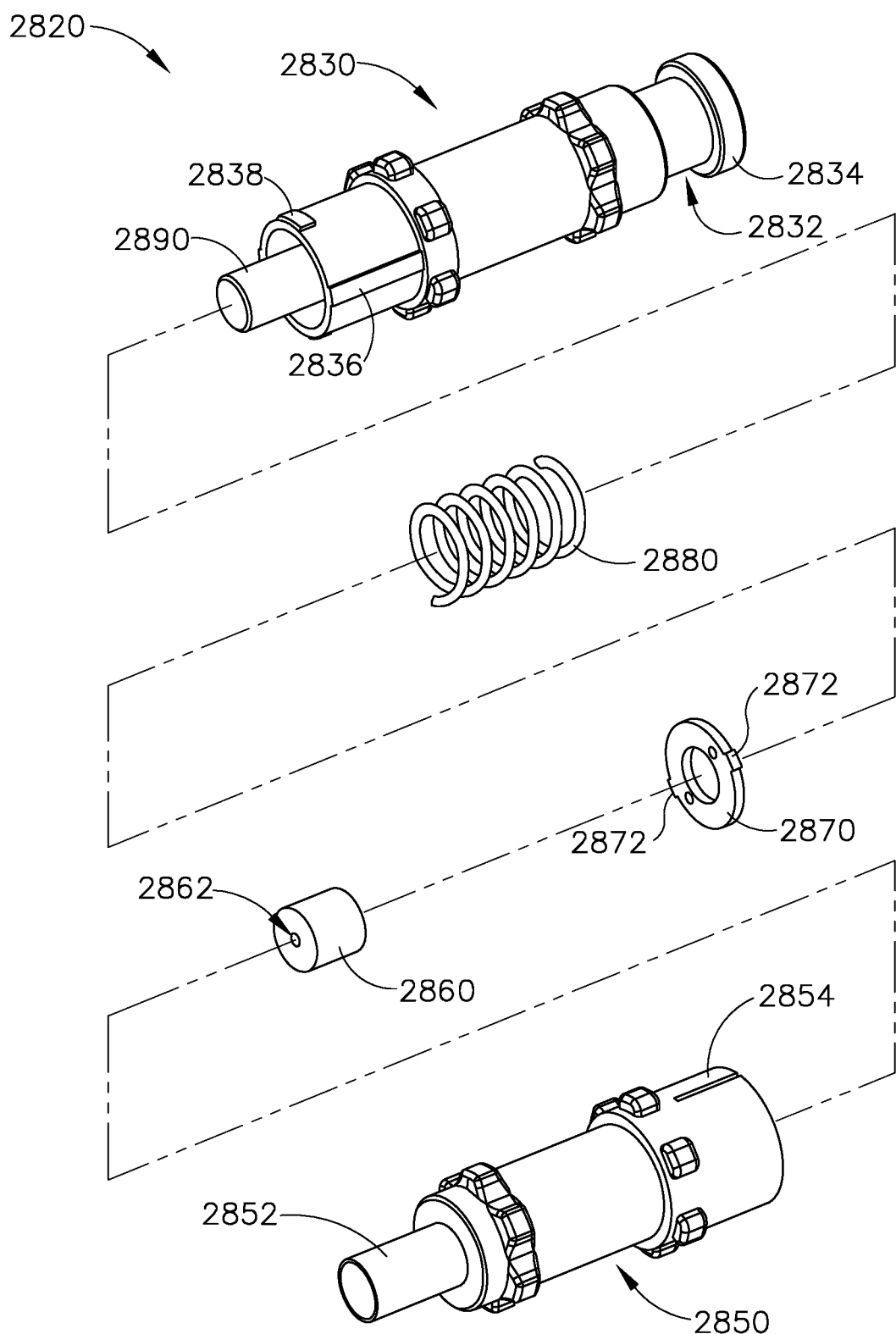
FIG. 30 depicts an exploded perspective view of the guidewire actuation mechanism of FIG. 29.

As shown in FIGS. 29-30, guidewire actuation mechanism (2820) comprises a first member (2850), a second member (2830), gripping member (2860), a retainer (2870), and a coil spring (2880), all of which are coaxially aligned with each other. In some versions, first member (2850) is positioned distally relative to second member (2830). In some other versions, first member (2850) is positioned proximally relative to second member (2830). In the present example, first and second members (2850, 2830) are configured to rotate together unitarily; while first and second members (2850, 2830) are configured to translate longitudinally relative to each other. In some versions, guidewire actuation assembly (2800) is configured to enable first member (2850) to translate longitudinally while holding second member (2830) longitudinally stationary. In some other versions, guidewire actuation assembly (2800) is configured to enable second member (2830) to translate longitudinally while holding first member (2850) longitudinally stationary.

Figure 31:
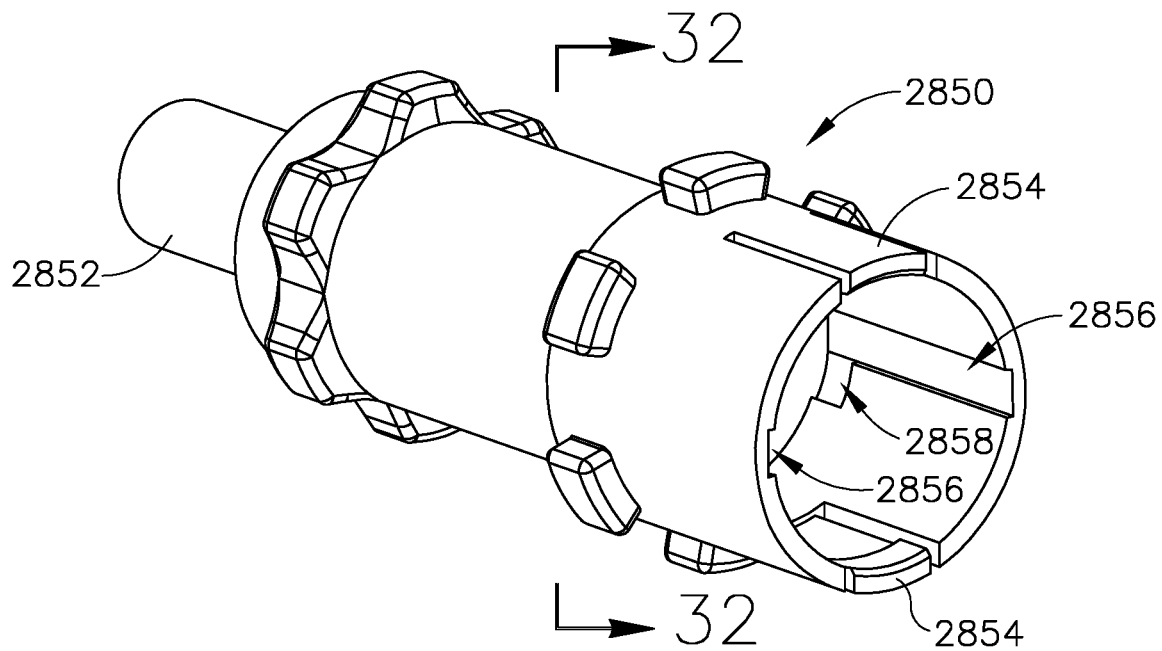
FIG. 31 depicts a perspective view of a first member of the guidewire actuation mechanism of FIG. 30.
Figure 32:
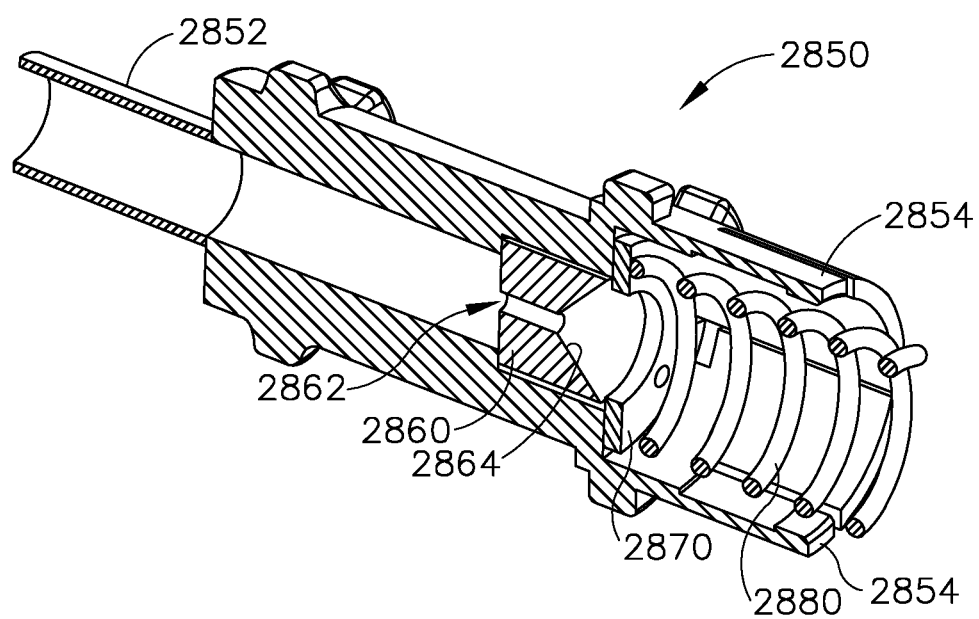
FIG. 32 depicts a cross-sectional view of the first member of FIG. 31, taken along line 32-32 of FIG. 31, with additional components of the guidewire actuation mechanism of FIG. 29 also shown.
Figure 33:
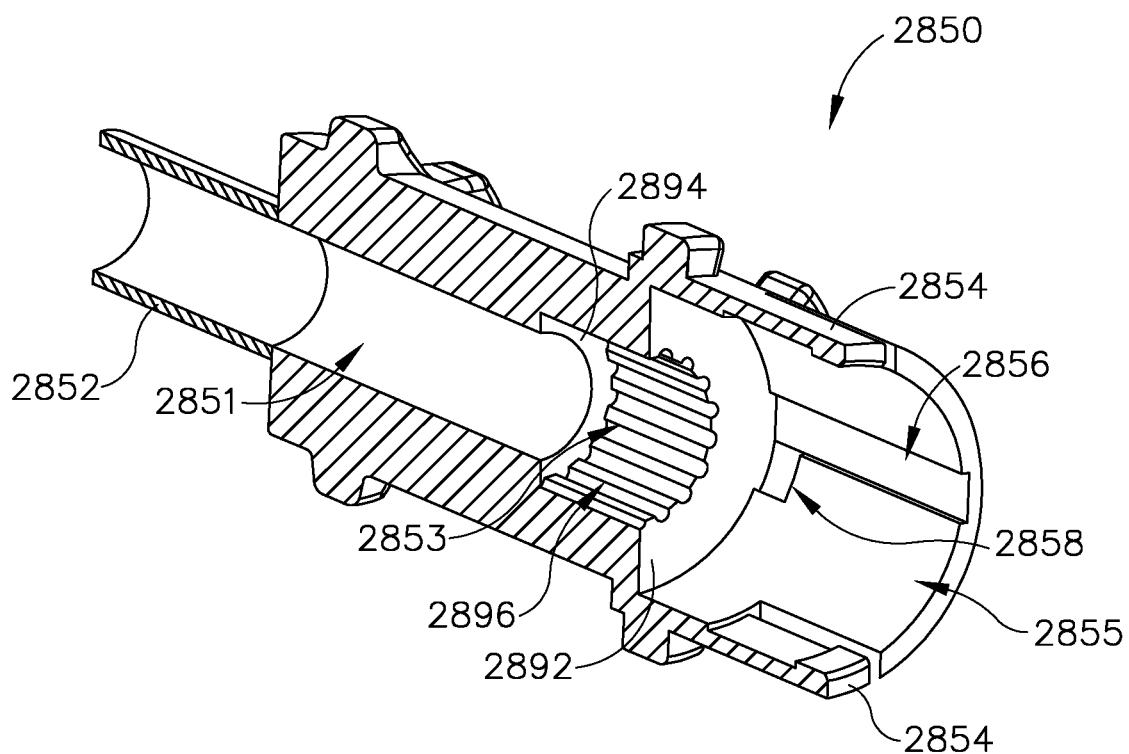
FIG. 33 depicts a cross-sectional view of the first member of FIG. 31, taken along line 32-32 of FIG. 31, with the additional components of FIG. 32 omitted.

As shown in FIGS. 31-33, first member (2850) includes a mount member (2852), a pair of latch arms (2854), a pair of keyways (2856), and a pair of retainer recesses (2858). As best shown in FIG. 32, gripping member (2860) comprises a cylindraceous body (2860) that defines a central bore (2862) and frusto-conical lead-in surface (2864) that leads into central bore (2862). Gripping member (2860) of the present example is formed of an elastomeric material (e.g., silicone, rubber, etc.) and is resiliently biased to assume a configuration where central bore (2862) has a diameter that is less than the outer diameter of elongate member (802). Thus, gripping member (2860) is resiliently biased to assume a configuration where gripping member (2860) will grip an elongate member (802) that is disposed in central bore (2862). However, as will be described in greater detail below, gripping member (2860) may be compressed longitudinally, which will effectively enlarge the diameter of central bore (2862), which will allow gripping member (2860) to release an elongate member (802) that is disposed in central bore (2862).

Gripping member (2860) is positioned in second bore region (2853). Gripping member (2860) is slightly press-fit into second bore region (2853), such that the outer sidewall of gripping member (2860) bears against splined surface (2896). The configuration of splined surface (2896) and gripping member (2860), as well as the elastomeric properties of gripping member (2860), prevent gripping member (2860) from rotating within second bore region (2853).

Retainer (2870) is configured to fit against first shoulder surface (2892) and an end of gripping member (2860), such that gripping member (2860) is longitudinally captured between retainer (2870) and second shoulder surface (2894). Retainer (2870) includes a pair of outwardly extending tabs (2872) (FIG. 30), which are angularly spaced 180 degrees apart from each other and are configured to fit in retainer recesses (2858) of first member (2850). Tabs (2872) (FIG. 30) and retainer recesses (2858) thus cooperate to retain retainer (2870) in first member (2850).

First member (2850) defines a first bore region (2851), a second bore region (2853), and a third bore region (2855). Second bore region (2853) has a diameter that is larger than the diameter of first bore region (2851); and third bore region (2855) has a diameter that is larger than the diameter of second bore region (2853). The interior of first member (2850) further includes a first shoulder surface (2892), a second shoulder surface (2894), and an inner splined surface (2896) extending longitudinally between shoulder surfaces (2892, 2894) along second bore region (2853). Latch arms (2854), keyways (2856), and retainer recesses (2858) are positioned along third bore region (2855).

Mount member (2852) of the present example is cylindraceous and is configured to slidably fit in first yoke (2814) (FIG. 28). First yoke (2814) (FIG. 28) is configured to support first member (2850) via mount member (2852) while still permitting guidewire actuation mechanism (2820) to rotate relative to slide actuator (2810). In some versions, first yoke (2814) (FIG. 28) also allows first member (2850) to translate longitudinally relative to first yoke (2814), as will be described in greater detail below. Mount member (2852) (FIG. 30) is longitudinally positioned to correspond with first bore region (2851).

Figure 34:
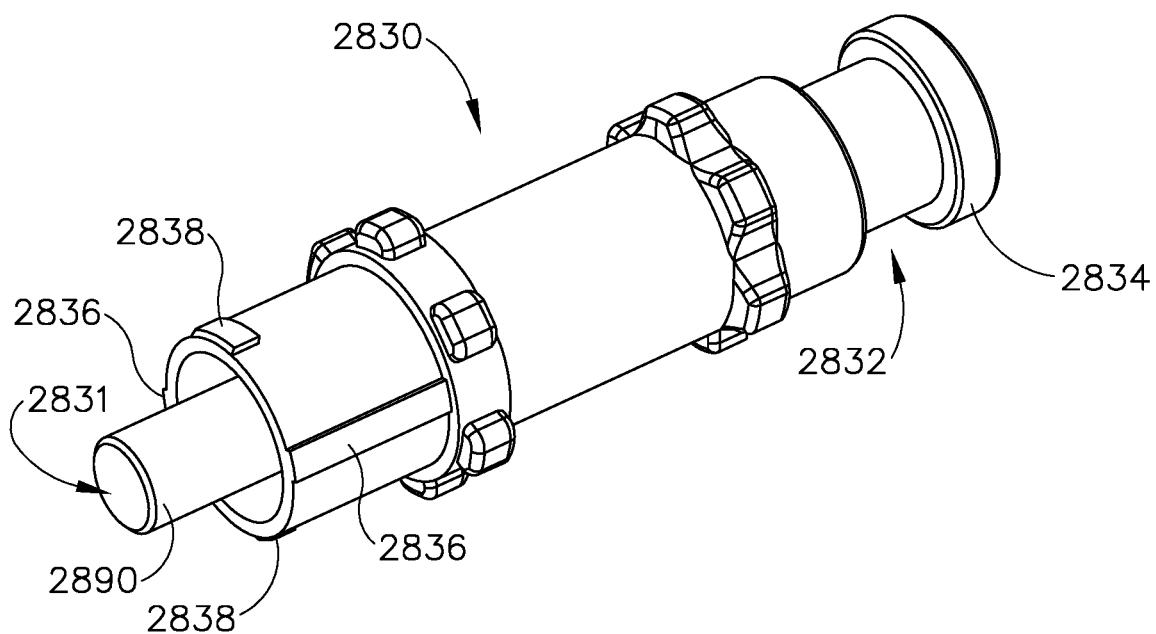
FIG. 34 depicts a perspective view of a second member of the guidewire actuation mechanism of FIG. 30.

As shown in FIG. 34, second member (2830) comprises an annular recess (2832), an annular flange (2834) adjacent to annular recess (2832), pair of longitudinally extending keys (2836), a pair of latch bosses (2838), and a plunger feature (2890). A central bore (2831) extends along the full length of second member (2830) and is configured to align with bore regions (2851, 2853, 2855) (FIG. 33) of first member (2850). Annular recess (2832) is configured for receipt in second yoke (2816) (FIG. 28). Second yoke (2816) (FIG. 28) is configured to support second member (2830) via annular recess (2832) while still permitting guidewire actuation mechanism (2820) (FIG. 28) to rotate relative to slide actuator (2810) (FIG. 28). In some versions, second yoke (2816) and annular recess (2832) are configured to allow second member (2830) to translate longitudinally relative to second yoke (2816), as will be described in greater detail below. In such versions, annular flange (2834) may nevertheless restrict translation of second member (2830) relative to second yoke (2816). In some other versions, second yoke (2816) and annular recess (2832) are configured to prevent second member (2830) from translating longitudinally relative to second yoke (2816). In such versions, first member (2850) is operable to translate longitudinally relative to first yoke (2814).

Keys (2836) of second member (2830) are angularly spaced 180 degrees apart from each other and are configured to slidably fit within corresponding keyways (2856) (FIG. 33) of first member (2850) (FIG. 33). Keys (2836) and keyways (2856) (FIG. 33) cooperate to prevent first and second members (2850, 2830) (FIGS. 33, 34) from rotating relative to each other; while allowing first and second members (2850, 2830) to translate relative to each other. Latch bosses (2838) of second member (2830) are angularly spaced 180 degrees apart from each other and are configured to engage corresponding latch arms (2854) (FIG. 33) of first member (2850). Latch bosses (2838) are configured to cooperate with latch arms (2854) to restrict translation of second member (2830) relative to first member (2850), thereby preventing inadvertent separation of second member (2830) from first member (2850). Coil spring (2880) is configured to fit in third bore region (2855) and resiliently bias first and second members (2850, 2830) longitudinally away from each other.

Figure 35A:
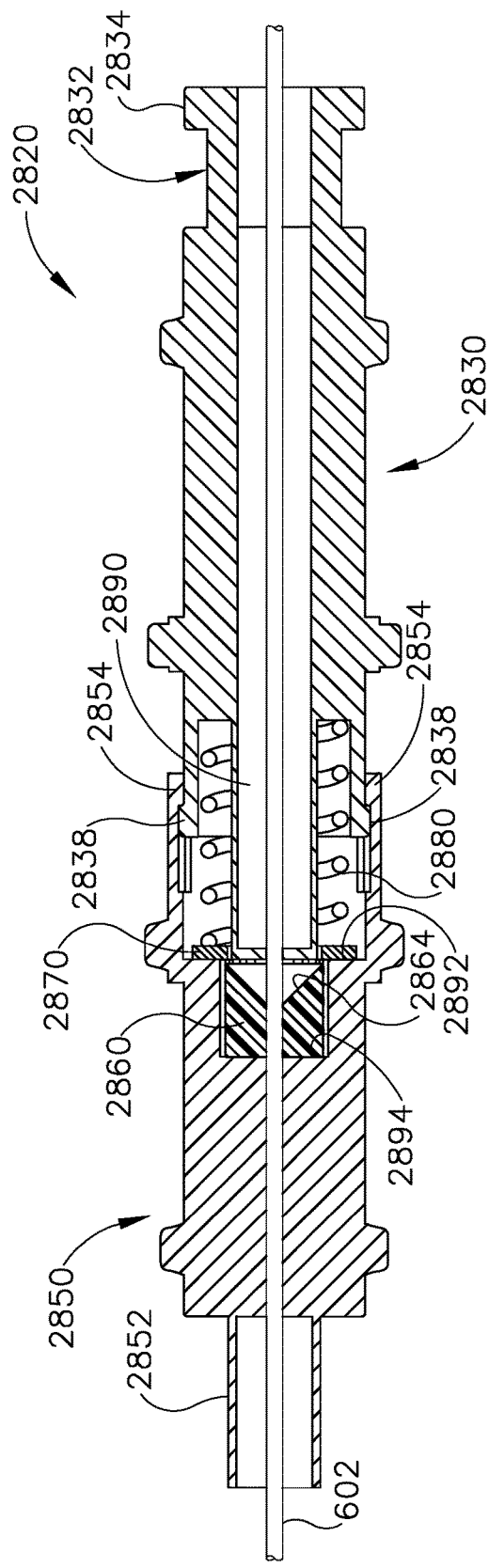
FIG. 35A depicts a cross-sectional view of the guidewire actuation mechanism of FIG. 29, with the guidewire actuation mechanism in a guidewire-gripping state.
Figure 35B:
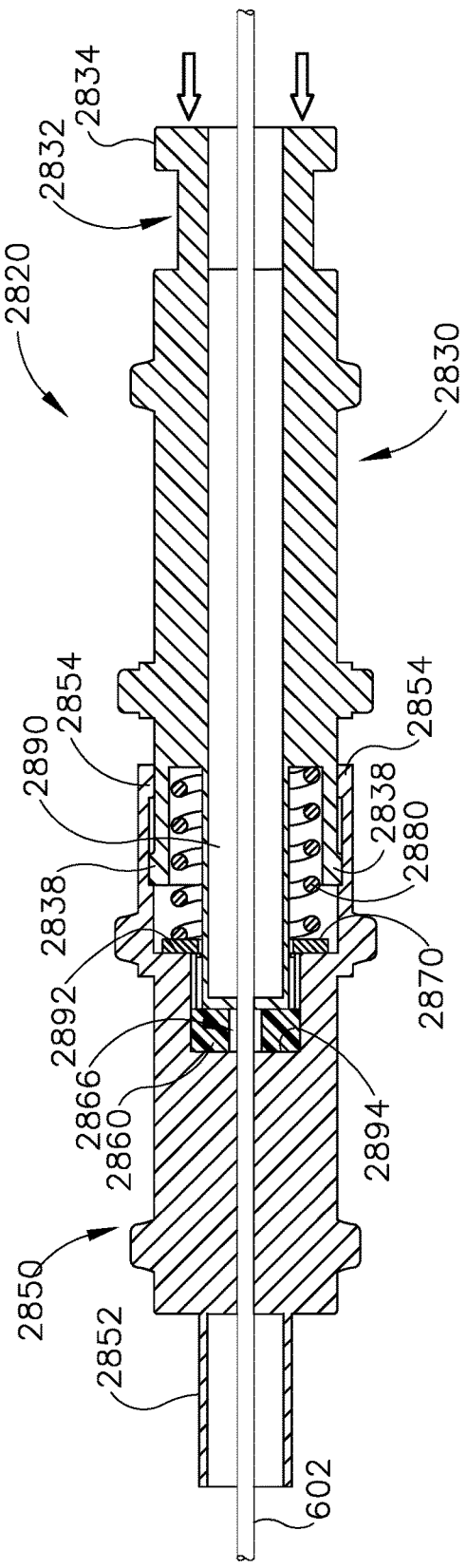
FIG. 35B depicts a cross-sectional view of the guidewire actuation mechanism of FIG. 29, with the second member actuated relative to the first member to transition the guidewire actuation mechanism to a guidewire-releasing state.

FIGS. 35A-35B show guidewire actuation mechanism (2820) transitioning between a locked state (FIG. 35A), in which gripping member (2860) firmly grips elongate member (802); and an unlocked state (FIG. 35B), in which gripping member (2860) releases elongate member (802). As shown in FIG. 35A, gripping member (2860) is in a non-compressed state such that gripping member (2860) maintains a firm grip on elongate member (802). Thus, as guidewire actuation mechanism (2820) is translated along the longitudinal axis of elongate member (802), guidewire actuation mechanism (2820) will drive elongate member (802) to translate along the longitudinal axis of elongate member (802). Similarly, as guidewire actuation mechanism (2820) is rotated about the longitudinal axis of elongate member (802), guidewire actuation mechanism (2820) will drive elongate member (802) to rotate about the longitudinal axis of elongate member (802).

FIG. 35B shows guidewire actuation mechanism (2820) being transitioned to the unlocked state by second member (2820) translating longitudinally while first member (2850) remains longitudinally stationary. As noted above, in some other versions, guidewire actuation mechanism (2820) may transition to the unlocked state by first member (2850) translating longitudinally while second member (2820) remains longitudinally stationary. In either case, when guidewire actuation mechanism (2820) is in the unlocked state, plunger feature (2890) bears against gripping member (2860) and thereby compresses gripping member (2860) against second shoulder surface (2894). This compression of gripping member (2860) enlarges the diameter of central bore (2862), thereby causing gripping member (2860) to release its grip on elongate member (802). FIG. 35B shows gripping member (2860) defining a gap around elongate member (802). In some other versions, a compressed gripping member (2860) may otherwise effectively release its grip on elongate member (802) without necessarily defining a gap around elongate member (802). In either case, with elongate member (802) released from gripping member (2860), the operator may pull elongate member (802) from guidewire actuation mechanism (2820) or otherwise adjust the longitudinal position of elongate member (802) relative to guidewire actuation mechanism (2820).

By way of example only, after achieving the unlocked state shown in FIG. 35B, the operator may wish to remove a first kind of elongate member (802) (e.g., an illuminating guidewire) and replace it with a second kind of elongate member (802) (e.g., a guidewire with a position sensor that cooperates with an IGS system). Once the operator has replaced the elongate member (802) or otherwise adjusted the longitudinal position of elongate member (802) relative to guidewire actuation mechanism (2820), the operator may release second member (2830) (or release first member (2850) in cases where the operator translated first member (2850) relative to second member (2830). The resilience of coil spring (2880) will return first and second members (2850, 2830) back to the relationship shown in FIG. 35A, such that plunger (2890) no longer compresses gripping member (2860). With gripping member (2860) no longer being compressed, central bore (2862) returns to its natural state with a smaller diameter, such that gripping member (2860) will again grip elongate member (802) after compression from plunger (2890) is removed. With guidewire actuation mechanism (2820) back in the locked state of FIG. 35A, the operator may again manipulate guidewire actuation assembly (2800) to translate elongate member (802) along the longitudinal axis of elongate member (802) and rotate elongate member (802) about the longitudinal axis of elongate member (802).

While the foregoing example describes guidewire actuation assembly (2800) as selectively gripping, translating, and rotating elongate member (802) in the form of a guidewire (602), a similar configuration may be used to selectively grip, translate, and rotate other kinds of devices. By way of example only, guidewire actuation assembly (2800) may be varied to accommodate an endoscope or other elongate instrument as will be apparent to those skilled in the art in view of the teachings herein.

While various examples described herein are provided in the context of instrumentation that is sized to pass through a paranasal sinus ostium, it should be understood that this is just a merely illustrative example. The teachings herein may be readily applied in the context of instrumentation that is positioned anywhere within a patient's head; or elsewhere within a patient's anatomy. Other examples of anatomical structures that may be reached by instrumentation configured in accordance with the teachings herein include, but are not limited to, cranial nerves, vidian nerves, etc. Still other examples of anatomical structures that may be reached by instrumentation configured in accordance with the teachings herein will be apparent to those skilled in the art in view of the teachings herein.

V. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus for use with an elongate member, the apparatus comprising: (a) an engagement member; (b) a hollow shaft extending from the engagement member along a longitudinal axis; (c) a compression element supported by the hollow shaft, wherein the compression element is radially movable relative to the hollow shaft; (d) a resilient gripping member disposed within the hollow shaft, wherein the resilient gripping member is configured to slidably receive the elongate member therethrough along the longitudinal axis, wherein the compression element is positioned to confront a radially outer surface of the resilient gripping member; and (e) a compression member slidably disposed over the hollow shaft, includes an inner surface configured to engage the compression element as the compression member advances from the unlocked position toward the locked position, wherein the inner surface has a plurality of detent features configured to engage the compression element in the locked position with different sized elongate members, wherein the compression member is operable to selectively translate longitudinally along the hollow shaft between a locked position and an unlocked position, wherein in the locked position the compression member is configured to urge the compression element radially against the resilient gripping member such that the resilient gripping member deforms radially inwardly to grip the elongate member and thereby prohibit translation of the elongate member through the apparatus, wherein in the unlocked position the compression member is configured to permit the compression element and the resilient gripping member to move radially away from the elongate member and thereby permit translation of the elongate member through the apparatus.

Example 2

The apparatus of Example 1, wherein the resilient gripping member is configured to secure the elongate member axially and rotationally relative to the apparatus when the compression member is in the locked position, wherein the resilient gripping member is configured to permit the elongate member to freely translate and rotate therethrough when the compression member is in the unlocked position.

Example 3

The apparatus of Example 2, wherein the engagement member, the hollow shaft, the compression element, the resilient gripping member, and the compression member are configured to rotate together about the longitudinal axis.

Example 4

The apparatus of any one or more of Examples 2 through 3, wherein the compression element is configured to overlie the resilient gripping member in the locked position.

Example 5

The apparatus of Example 4, wherein the compression element comprises a ball, wherein a sidewall of the hollow shaft includes an aperture that movably receives the ball therein.

Example 6

The apparatus of Example 4, wherein the compression element comprises a flexible arm, wherein a base end of the flexible arm is fixed relative to the hollow shaft.

Example 7

The apparatus of any one or more of Examples 5 through 6, wherein the compression member comprises a plurality of compression members arranged circumferentially about the hollow shaft.

Example 8

The apparatus of Example 6, wherein the hollow shaft includes the flexible arm.

Example 9

The apparatus of Example 8, wherein the flexible arm includes an arcuate projection configured to engage one of the detent features.

Example 10

The apparatus of any one or more of the Examples 1 through 9, further comprising a support structure having a first end portion and a second end portion, wherein the first end portion supports a first end of a first coupling member, wherein the second end portion supports the second end of the second coupling member.

Example 11

An instrument comprising: (a) a handle assembly; and (b) the apparatus of Example 10, wherein the support structure is slidably coupled to the handle assembly.

Example 12

The instrument of Example 11, further comprising a guide catheter extending distally from the handle assembly.

Example 13

The instrument of Example 12, further comprising a dilation catheter slidably disposed relative to the guide catheter.

Example 14

The instrument of Example 13, further comprising an elongate member slidably disposed within one or both of the guide catheter or the dilation catheter.

Example 15

The instrument of Example 14, wherein the elongate member comprises a guidewire.

Example 16

The instrument of Example 14, wherein the elongate member is sized to pass through a paranasal sinus ostium of a patient.

Example 17

An apparatus for use with an elongate member, the apparatus comprising: (a) an engagement member; (b) a hollow shaft extending from the engagement member along a longitudinal axis; (c) a compression element supported by the hollow shaft, wherein the compression element is movable radially relative to the hollow shaft; (d) a resilient gripping member disposed within the hollow shaft, wherein the resilient gripping member is configured to slidably receive the elongate member therethrough along the longitudinal axis, wherein the compression element is positioned to confront a radially outer surface of the resilient gripping member; and (e) a collar slidably disposed over the hollow shaft, wherein the collar is operable to selectively translate longitudinally along the hollow shaft between a locked position and an unlocked position, wherein the collar includes a conical inner surface configured to engage the compression element as the collar advances from the unlocked position toward the locked position wherein the conical inner surface has a set of detent features configured to engage the compression element in the locked position with different sized elongate members, wherein in the locked position the collar is configured to urge the compression element radially against the resilient gripping member such that the resilient gripping member deforms radially inwardly to grip the elongate member and thereby prohibit translation of the elongate member through the apparatus, wherein in the unlocked position the collar is configured to permit the compression element and the resilient gripping member to move radially away from the elongate member and thereby permit translation of the elongate member through the apparatus.

Example 18

The apparatus of Example 17, wherein the compression element is spherical, wherein a sidewall of the hollow shaft includes an aperture that movably receives the compression element therein.

Example 19

An apparatus for use with an elongate member, the apparatus comprising: (a) an engagement member; (b) a hollow shaft extending from the engagement member along a longitudinal axis, wherein the hollow shaft includes a cantilever arm, wherein the cantilever arm has a base end fixed relative to the hollow shaft; (c) a cantilever arm supported by the hollow shaft, wherein the cantilever arm is movable radially relative to the hollow shaft; (d) a resilient gripping member disposed within the hollow shaft, wherein the resilient gripping member is configured to slidably receive the elongate member therethrough along the longitudinal axis, wherein the compression element is positioned to confront a radially outer surface of the resilient gripping member; and (e) a collar slidably disposed over the hollow shaft, wherein the collar is operable to selectively translate longitudinally along the hollow shaft between a locked position and an unlocked position, wherein the collar includes a conical inner surface configured to engage the compression element as the collar advances from the unlocked position toward the locked position wherein the conical inner surface has a detent feature configured to engage the compression element in the locked position with different sized guidewires, wherein in the locked position the collar urges the compression element radially against the resilient gripping member such that the resilient gripping member deforms radially inwardly to grip the elongate member and thereby prohibit translation of the elongate member through the apparatus, wherein in the unlocked position the collar permits the compression element and the resilient gripping member to move radially away from the elongate member and thereby permit translation of the elongate member through the apparatus.

Example 20

The apparatus of Example 19, wherein the cantilever arm has an arcuate projection configured to engage the detent feature.

Example 21

An apparatus for use with a dilation instrument having a flexible instrument, the apparatus comprising: (a) a first coupling member, wherein the first coupling member includes: (i) a first end, (ii) a second end, and (iii) a first through bore extending between the first end and the second end of the first coupling member; (b) a second coupling member configured to releasably couple with the first coupling member, wherein the second coupling member includes: (i) a first end, (ii) a second end, and (iii) a second through bore extending between the first end and the second end of the second coupling member, wherein the first through bore and the second through bore are sized to receive a flexible instrument axially therethrough; and (c) a compressible body disposed in the first coupling member, wherein the compressible body defines a bore configured to align coaxially with the first through bore and the second through bore to receive the flexible instrument axially therethrough, wherein the compressible body is resiliently biased toward an expanded state in which the flexible instrument is freely translatable through the first and second coupling members and the compressible body, wherein the compressible body is configured to compress radially inwardly in response to relative rotation between the first and second coupling members to frictionally engage the flexible instrument and thereby fix the flexible instrument relative to the first and second coupling members.

Example 22

The apparatus of Example 21, wherein the first coupling member includes a first threaded portion, wherein the second coupling member includes a second threaded portion configured to threadedly engage the first threaded portion when the first coupling member rotates relative to the second coupling member.

Example 23

The apparatus of Example 22, wherein the first threaded portion includes external threads and the second threaded portion includes internal threads.

Example 24

The apparatus of any one or more of Examples 21 through 23, wherein the second coupling member further comprises a projection, wherein the projection is configured to compress the compressible body in response to relative rotation between the first coupling member and the second coupling member.

Example 25

The apparatus of Example 24, wherein the first coupling member includes a conical shaped surface, wherein in response to relative rotation between the first and second coupling members the projection is configured to compress the compressible body axially against the conical shaped surface such that the compressible body deforms radially inwardly against the flexible instrument.

Example 26

The apparatus of any one or more of Examples 24 through 25, wherein the second coupling member includes a counterbore, wherein the projection is disposed within the counterbore.

Example 27

The apparatus of any one or more of Examples 21 through 26, wherein the first and second coupling members are tubular in shape.

Example 28

The apparatus of any one or more of Examples 21 through 27, wherein the second end of the first coupling member is configured to threadedly engage the first end of the second coupling member, wherein the compressible body is disposed at the second end of the first coupling member.

Example 29

The apparatus of any one or more of Examples 21 through 28, further comprising a support structure having a first end portion and a second end portion, wherein the first end portion supports the first end of the first coupling member, wherein the second end portion supports the second end of the second coupling member.

Example 30

The apparatus of Example 29, wherein the first end portion is configured to allow rotation of the first coupling member relative to the support structure, wherein the second end portion is configured to allow rotation of the second coupling member relative to the support structure.

Example 31

The apparatus of any one or more of Examples 29 through 30, wherein either: (i) the first end portion is configured to allow axial movement of the first coupling member relative to the support structure, or (ii) the second end portion is configured to allow axial movement of the second coupling member relative to the support structure.

Example 32

An instrument comprising: (a) a handle assembly; and (b) the apparatus of any one or more of Examples 29 through 31, wherein the support structure is slidably coupled to the handle assembly.

Example 33

The instrument of Example 32, further comprising a guide catheter extending distally from the handle assembly.

Example 34

The instrument of Example 33, further comprising a dilation catheter slidably disposed within the guide catheter.

Example 35

The instrument of Example 34, further comprising a flexible instrument slidably disposed within the dilation catheter, wherein the flexible instrument comprises a guidewire.

Example 36

The instrument of Example 35, wherein the flexible instrument comprises a guidewire.

Example 37

The instrument of Example 36, wherein the flexible instrument is sized to pass through a paranasal sinus ostium of a patient.

Example 38

An apparatus comprising: (a) a body; (b) a shaft assembly extending distally from the body; (c) a flexible instrument slidably disposed within the shaft assembly; and (d) a flexible instrument actuation assembly configured to actuate the flexible instrument through the shaft assembly, wherein the flexible instrument actuation assembly comprises: (i) a support structure, and (ii) an actuator mounted to the support structure, wherein the actuator comprises: (A) a first coupling member having a first through bore, (B) a second coupling member configured to releasably couple with the first coupling member, wherein the second coupling member includes a second through bore, wherein the flexible instrument is configured to extend axially through the first through bore and the second through bore, and (C) a gripping member, wherein the gripping member is configured to transition between a first state and a second state in response to relative rotation between the first and second coupling members, wherein in the first state the gripping member permits the flexible instrument to freely translate through the actuator, wherein in the second state the gripping member frictionally engages the flexible instrument and fixes the flexible instrument relative to the actuator.

Example 39

The apparatus of Example 38, wherein the first coupling member includes a first threaded portion, wherein the second coupling member includes a second threaded portion configured to threadedly engage the first threaded portion in response to relative rotation between the first and second coupling members.

Example 40

The apparatus of any one or more of Examples 38 through 39, wherein the first coupling member includes a conical shaped surface, wherein the second coupling member includes a projection, wherein in response to relative rotation between the first and second coupling members the projection is configured to compress the compressible body axially against the conical shaped surface such that the compressible body deforms radially inwardly against the flexible instrument.

Example 41

An apparatus for use with a dilation instrument having a flexible instrument, the apparatus comprising: (a) a first coupling member, wherein the first coupling member comprises: (i) a first end, (ii) a threaded second end, and (iii) a first through bore extending between the first end and the second end of the first coupling member; (b) a second coupling member configured to releasably couple with the first coupling member, wherein the second coupling member comprises: (i) a threaded first end, (ii) a second end, and (iii) a second through bore extending between the first end and the second end of the second coupling member, wherein the first through bore and the second through bore are sized to receive a flexible instrument axially therethrough, wherein the flexible instrument is sized to pass through a paranasal sinus ostium of a patient; and (c) a compressible body disposed in the first coupling member, wherein the compressible body defines a bore configured to align coaxially with the first through bore and the second through bore to receive the flexible instrument axially therethrough, wherein the compressible body is resiliently biased toward an expanded state in which the flexible instrument is freely translatable through the first and second coupling members and the compressible body, wherein the compressible body is configured to compress radially inwardly in response to threaded engagement of the threaded second end of the first coupling member with the threaded first end of the second coupling member, wherein when compressed the compressible body is configured to frictionally engage the flexible instrument and thereby fix the flexible instrument relative to the first and second coupling members.

Example 42

The apparatus of Example 41, wherein the first coupling member includes a conical shaped surface, wherein the second coupling member includes a projection, wherein in response to relative rotation between the first and second coupling members the projection is configured to compress the compressible body axially against the conical shaped surface such that the compressible body deforms radially inwardly against the flexible instrument.

Example 43

A method of operating a flexible instrument actuation assembly of a dilation instrument, wherein the flexible instrument actuation assembly includes a first elongate member, a second elongate member, and a gripping member arranged therebetween, the method comprising: (a) providing the first elongate member in a first rotational state relative to the second elongate member; (b) translating a flexible instrument through the first elongate member and the second elongate member while the first elongate member is in the first rotational state; and (c) rotating the first elongate member relative to the second elongate member toward a second rotational state in which the gripping member frictionally engages the flexible instrument and prevents further translation of the flexible instrument relative to the first and second elongate members.

Example 44

The method of Example 43, wherein the gripping member comprises a compressible body, wherein rotating the first elongate member relative to the second elongate member comprises compressing the compressible body so that the compressible body frictionally engages the flexible instrument.

Example 45

An apparatus, comprising: (a) a first elongate member defining a first bore, wherein the first bore of the first elongate member is sized to receive a guidewire; (b) a second elongate member defining a second bore, wherein the second bore of the second elongate member is coaxially aligned with the first bore of the first elongate member and is sized to receive a guidewire, the second elongate member further includes a projection positioned in the first bore of the first elongate member; and (c) a compressible body disposed in the first bore of the first elongate member, wherein the compressible body defines a third bore, wherein the compressible body is resiliently biased to define a first inner diameter in the third bore of the compressible body, wherein the projection of the second elongate member is configured to deform the compressible body in response to relative translation between the first and second elongate members, wherein the compressible body is configured to define a second inner diameter in the third bore of the compressible body in response to deformation by the projection of the second elongate member, wherein the second inner diameter is larger than the first inner diameter, wherein the compressible body is configured to grip the guidewire in the third bore of the compressible body when the third bore has the first inner diameter, wherein the compressible body is configured to release the guidewire in the third bore of the compressible body when the third bore of the compressible body has the second inner diameter.

Example 46

The apparatus of Example 45, further comprising a frame having a first end portion and a second end portion, wherein the first end portion supports an end of the first elongate member, wherein the second end portion supports an end of the second elongate member.

Example 47

The apparatus of Example 46, wherein the first end portion is configured to allow rotation of the first elongate member relative to the frame, wherein the second end portion is configured to allow rotation of the second elongate member relative to the frame.

Example 48

The apparatus of any one or more of Examples 46 through 47, wherein either: (i) the first end portion is configured to allow translation of the first elongate member relative to the frame, or (ii) the second end portion is configured to allow translation of the second elongate member relative to the frame.

Example 49

The apparatus of any one or more of Examples 46 through 48, further comprising a handle assembly, wherein the frame is slidably secured to the handle assembly such that the frame is configured to provide translation of the first and second elongate members relative to the handle assembly.

Example 50

The apparatus of Example 49, further comprising a guide catheter extending distally from the handle assembly.

Example 51

The apparatus of Example 50, further comprising a dilation catheter slidably disposed in the guide catheter.

Example 52

The apparatus of Example 51, further comprising a guidewire slidably disposed in the dilation catheter, wherein the guidewire is secured to the first and second elongate members via the compressible body.

Example 53

The apparatus of any one or more of Examples 45 through 51, further comprising a guidewire secured to the first and second elongate members via the compressible body.

Example 54

The apparatus of Example 53, wherein the guidewire is configured to pass through an ostium of a paranasal sinus of a human.

Example 55

The apparatus of any one or more of Examples 45 through 54, further comprising a resilient member configured to urge the first and second elongate members away from each other.

Example 56

The apparatus of Example 55, further comprising a boss structure configured to restrict displacement of the first and second elongate members away from each other.

Example 57

The apparatus of any one or more of Examples 45 through 56, wherein the compressible body is cylindraceous.

Example 58

The apparatus of Example 57, wherein the first bore of the first member includes gripping features configured to engage the compressible body and thereby prevent rotation of the compressible body relative to the first member.

Example 59

The apparatus of any one or more of Examples 45 through 58, wherein the compressible body is elastomeric.

Example 60

An apparatus, comprising: (a) a guidewire, wherein a distal portion of the guidewire is sized to fit through an anatomical passageway within a head of a human; and (b) an actuator assembly, wherein the actuator assembly comprises: (i) a first tubular member, (ii) a second tubular member, wherein a free end of the second tubular member is positioned within the first tubular member, wherein the first and second tubular members are configured to transition between a locking state and an unlocking state, and (iii) an elastomeric body positioned within the first tubular member, wherein the guidewire is positioned in a bore of the elastomeric body, wherein the elastomeric body is configured to transition between a gripping state and a releasing state, wherein the elastomeric body is configured to firmly grip the guidewire in the gripping state, wherein the elastomeric body is configured to allow the guidewire to translate along the bore in the releasing state, wherein the compressible body is configured to maintain the gripping state when the first and second tubular members are in the locking state, wherein the free end of the second tubular member is configured to drive the compressible body from the gripping state to the releasing state when the first and second tubular members are transitioned from the locking state to the unlocking state.

Example 61

The apparatus of Example 60, wherein the first and second tubular members together define a first length in the locking state, wherein the first and second tubular members together define a second length in the unlocking state.

Example 62

The apparatus of Example 61, wherein the second length is less than the first length.

Example 63

A method, comprising: (a) engaging an actuator assembly while the actuator assembly is in a first state, wherein the actuator assembly includes: (i) a first elongate member, (ii) a second elongate member, and (iii) an elastomeric cylindraceous body, wherein the elastomeric cylindraceous body firmly grips a guidewire while the actuator assembly is in the first state; (b) translating the first elongate member relative to the second elongate member to transition the actuator assembly to a second state, wherein translation of the first elongate member relative to the second elongate member causes deformation of the elastomeric cylindraceous body, wherein the deformed elastomeric cylindraceous body at least partially releases the guidewire; and (c) translating the guidewire relative to the actuator assembly while the actuator assembly is in the second state.

Example 64

The method of Example 63, further comprising inserting a distal end of the guidewire into a Eustachian tube of a human or into an ostium of a paranasal sinus of a human.

VI. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein in its entirety.

It should be understood that any one or more of the teachings, expressions, embodiments, examples, etc.

described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/ replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus for use with an elongate member, the apparatus comprising:
    (a) an engagement member;
    (b) a hollow shaft extending from the engagement member along a longitudinal axis;
    (c) a compression element supported by the hollow shaft, wherein the compression element is radially movable relative to the hollow shaft;
    (d) a resilient gripping member disposed within the hollow shaft, wherein the resilient gripping member is configured to slidably receive the elongate member therethrough along the longitudinal axis, wherein the compression element is positioned to confront a radially outer surface of the resilient gripping member; and
    (e) a compression member slidably disposed over the hollow shaft, including an inner surface configured to engage the compression element as the compression member advances from an unlocked position toward a first locked position, and further toward a second locked position, wherein the inner surface has a plurality of detent features configured to engage the compression element in the first locked position with a larger sized elongate member, and in the second locked position with a smaller sized elongate member, wherein the compression member is operable to selectively translate longitudinally along the hollow shaft between the first locked position, the second locked position and the unlocked position,
    wherein in the first locked position the compression member is configured to urge the compression element radially against the resilient gripping member such that the resilient gripping member deforms radially inwardly to grip the larger sized elongate member and thereby prohibit translation of the larger sized elongate member through the apparatus,
    wherein in the second locked position the compression member is configured to urge the compression element radially against the resilient gripping member such that the resilient gripping member deforms further radially inwardly relative to the first locked position to grip the smaller sized elongate member and thereby prohibit translation of the smaller sized elongate member through the apparatus,
    wherein in the unlocked position the compression member is configured to permit the compression element and the resilient gripping member to move radially away from the elongate member and thereby permit translation of the larger or smaller sized elongate members through the apparatus.

2. The apparatus of claim 1, wherein the resilient gripping member is configured to secure the elongate member axially and rotationally relative to the apparatus when the compression member is in the locked position, wherein the resilient gripping member is configured to permit the elongate member to freely translate and rotate therethrough when the compression member is in the unlocked position.

3. The apparatus of claim 2, wherein the engagement member, the hollow shaft, the compression element, the resilient gripping member, and the compression member are configured to rotate together about the longitudinal axis.

4. The apparatus of claim 3, wherein the compression element is configured to overlie the resilient gripping member in the locked position.

5. The apparatus of claim 4, wherein the compression element comprises a ball, wherein a sidewall of the hollow shaft includes an aperture that movably receives the ball therein.

6. The apparatus of claim 4, wherein the compression element comprises a flexible arm, wherein a base end of the flexible arm is fixed relative to the hollow shaft.

7. The apparatus of claim 6, wherein the compression member comprises a plurality of compression members arranged circumferentially about the hollow shaft.

8. The apparatus of claim 6, wherein the hollow shaft includes the flexible arm.

9. The apparatus of claim 8, wherein the flexible arm includes an arcuate projection configured to engage one of the detent features.

10. The apparatus of claim 9, further comprising a support structure having a first end portion and a second end portion, wherein the first end portion supports a first end of a first coupling member, wherein the second end portion supports a second end of a second coupling member.

11. An instrument comprising:
(a) a handle assembly; and
(b) the apparatus of claim 9, wherein the support structure is slidably coupled to the handle assembly.

12. The instrument of claim 11, further comprising a guide catheter extending distally from the handle assembly.

13. The instrument of claim 12, further comprising a dilation catheter slidably disposed relative to the guide catheter.

14. The instrument of claim 13, further comprising an elongate member slidably disposed within the one and/or both of the guide catheter or dilation catheter.

15. The instrument of claim 14, wherein the elongate member comprises a guidewire.

16. An apparatus for use with an elongate member, the apparatus comprising:
(a) an engagement member;
(b) a hollow shaft extending from the engagement member along a longitudinal axis;
(c) a compression element supported by the hollow shaft, wherein the compression element comprises a flexible arm, wherein a base end of the flexible arm is fixed relative to the hollow shaft, wherein the compression element is radially movable relative to the hollow shaft;
(d) a resilient gripping member disposed within the hollow shaft, wherein the resilient gripping member is configured to slidably receive the elongate member therethrough along the longitudinal axis, wherein the compression element is positioned to confront a radially outer surface of the resilient gripping member; and
(e) a compression member slidably disposed over the hollow shaft, including an inner surface configured to engage the compression element as the compression member advances from an unlocked position toward a locked position, wherein the inner surface has a plurality of detent features configured to engage the compression element in the locked position with different sized elongate members, wherein the compression member is operable to selectively translate longitudinally along the hollow shaft between the locked position and the unlocked position,
wherein in the locked position the compression member is configured to urge the compression element radially against the resilient gripping member such that the resilient gripping member deforms radially inwardly to grip the elongate member and thereby prohibit translation of the elongate member through the apparatus,
wherein in the unlocked position the compression member is configured to permit the compression element and the resilient gripping member to move radially away from the elongate member and thereby permit translation of the elongate member through the apparatus.

17. The apparatus of claim 16, wherein the resilient gripping member is configured to secure the elongate member axially and rotationally relative to the apparatus when the compression member is in the locked position, wherein the resilient gripping member is configured to permit the elongate member to freely translate and rotate therethrough when the compression member is in the unlocked position.

18. The apparatus of claim 17, wherein the engagement member, the hollow shaft, the compression element, the resilient gripping member, and the compression member are configured to rotate together about the longitudinal axis.

19. An apparatus for use with an elongate member, the apparatus comprising:
(a) an engagement member including a proximal end configured to be rotatably supported by a support structure;
(b) a hollow shaft extending from the engagement member along a longitudinal axis, wherein the hollow shaft including a distal end configured to be rotatably supported by the support structure;
(c) a compression element supported by the hollow shaft, wherein the compression element is radially movable relative to the hollow shaft;
(d) a resilient gripping member disposed within the hollow shaft, wherein the resilient gripping member is configured to slidably receive the elongate member therethrough along the longitudinal axis, wherein the compression element is positioned to confront a radially outer surface of the resilient gripping member; and
(e) a compression member slidably disposed over the hollow shaft, including an inner surface configured to engage the compression element as the compression member advances from an unlocked position toward a locked position, wherein the inner surface has a plurality of detent features configured to engage the compression element in the locked position with different sized elongate members, wherein the compression member is operable to selectively translate longitudinally along the hollow shaft between the locked position and the unlocked position,
wherein in the locked position the compression member is configured to urge the compression element radially against the resilient gripping member such that the resilient gripping member deforms radially inwardly to grip the elongate member and thereby prohibit translation of the elongate member through the apparatus,
wherein in the unlocked position the compression member is configured to permit the compression element and the resilient gripping member to move radially away from the elongate member and thereby permit translation of the elongate member through the apparatus
wherein the engagement member, the hollow shaft, the compression element, the resilient gripping member, and the compression member are configured to rotate together about the longitudinal axis relative to the support structure.

20. The apparatus of claim 19, further comprising a support structure having a first end portion and a second end portion, wherein the first end portion supports a first end of a first coupling member, wherein the second end portion supports a second end of a second coupling member.

\* \* \* \* \*